(12) United States Patent
Williams et al.

(10) Patent No.: US 7,659,369 B2
(45) Date of Patent: Feb. 9, 2010

(54) NEMATODE ATP SYNTHASE SUBUNIT E POLYPEPTIDE

(75) Inventors: Deryck Jeremy Williams, St. Louis, MO (US); Brandy Salmon, Durham, NC (US); Andrew P. Kloek, St. Louis, MO (US)

(73) Assignee: Divergence, Inc., St. Louis, MO (US)

( * ) Notice: Subject to any disclaimer, the term of this patent is extended or adjusted under 35 U.S.C. 154(b) by 0 days.

(21) Appl. No.: 11/834,237

(22) Filed: Aug. 6, 2007

(65) Prior Publication Data

US 2008/0160595 A1 Jul. 3, 2008

Related U.S. Application Data

(62) Division of application No. 11/091,969, filed on Mar. 28, 2005, now abandoned, which is a division of application No. 10/160,362, filed on May 30, 2002, now Pat. No. 6,903,190.

(60) Provisional application No. 60/294,777, filed on May 31, 2001.

(51) Int. Cl.
*C07K 14/00* (2006.01)
(52) U.S. Cl. ..................................................... 530/350
(58) Field of Classification Search ........................ None
See application file for complete search history.

(56) References Cited

OTHER PUBLICATIONS

Colman, Res Immun 145:33-36, 1996.*
Abaza et al., J Prot Chem 11:433-444, 1992.*
Witkowski et al. (1999) Biochemistry 38:11643-11650.*
Database GenBank Accession No. JC1412, Sep. 30, 1993.*
Database GenBank Accession No. A44246, Jun. 10, 1993.*
Database GenBank Accession No. A39566, Jul. 10, 1992.*
Database GenBank Accession No. A61438, Oct. 7, 1994.*
Database GenBank Accession No. A03979, Nov. 14, 1983.*
Brenner (1999) Trends Genet 15 :132-133.*
Scott et al. (1999) Nat Genet 21:440-443.*
Branden et al. "Introduction to Protein Structure", Garland Publishing Inc., New York, 1991, p. 247.*
Allen et al., "Analysis of Genes Expressed at the Infective Larval Stage Validates Utility of . . . " Infect. Immun. 68:5454, 2000.
GenBank® Accession No. T23910; GI: 7506279; Harris, B., Oct. 15, 1999.
GenBank® Accession No. BE578834; GI:9829776; McCarter et al., created: Aug. 16, 2000; updated: May 10, 2001.
GenBank® Accession No. BF013478; GI:10713753; McCarter et al., created: Oct. 6, 2000; updated: May 10, 2001.
GenBank® Accession No. AW052324; GI:5914683; McCarter et al., created: Sep. 20, 1999; updated: May 10, 2001.
GenBank® Accession No. BF014969; GI:10715244; McCarter et al., created: Oct. 6, 2000; updated: May 9, 2001.
GenBank® Accession No. BF250434; GI:11180617; McCarter et al., created: Nov. 15, 2000; updated: May 10, 2001.
GenBank® Accession No. AW152691; GI:6200636; Allen et al., created: Nov. 3, 1999; updated: Aug. 28, 2000.
GenBank® Accession No. NP_009031; GI:6005717; Fujiwara et al., Nov. 2, 2000.
GenBank® Accession No. P29419; GI:461587; Higuti et al., Mar. 1, 2002.
GenBank® Accession No. AW773517; GI:7710479; McCarter et al., created: May 5, 2000; updated: May 10, 2001.
GenBank® Accession No. AA072471; GI:1592572; Williams, S.A., created: Oct. 3, 1996; updated: Dec. 12, 1996.
GenBank® Accession No. BG736353; GI:14086042; McCarter; Jul. 10, 2001.
GenBank® Accession No. BU094722; GI:22544284; McCarter; Jan. 9, 2003.

* cited by examiner

*Primary Examiner*—David J Steadman
(74) *Attorney, Agent, or Firm*—Fish & Richardson P.C.

(57) ABSTRACT

Nucleic acid molecules from nematodes encoding ATP synthase subunit E polypeptides are described. ATP synthase subunit E-like polypeptide sequences are also provided, as are vectors, host cells, and recombinant methods for production of ATP synthase subunit E-like nucleotides and polypeptides. Also described are screening methods for identifying inhibitors and/or activators, as well as methods for antibody production.

2 Claims, 4 Drawing Sheets

```
1
    gtt taa tta ccc aag ttt gag ata aaa ttt att taa aaa ATG TCA AAG CCG CAT CCG ACC
                                                        M   S   K   P   H   P   T
61
    GAT ATA ATT CTT CCT GAA CCA ATC CAG GTT TCA CCG TTA ATT CGT TTT GCT CGT TGG ACT
    D   I   I   L   P   E   P   I   Q   V   S   P   L   I   R   F   A   R   W   T
121
    GCT CTT GGT GCG GGA ATA ATT TAT GGC TAT GTT CGT TTC CAT CAA ATT GCT CGT GGT CAT
    A   L   G   A   G   I   I   Y   G   Y   V   R   F   H   Q   I   A   R   G   H
181
    GCA CTT ATT CGT GAA TGG GAG GCT GAT AAA TTT ATC CAT AAA GTT GAA CAG GAG CAT GAG
    A   L   I   R   E   W   E   A   D   K   F   I   H   K   V   E   Q   E   H   E
241
    AGA GCT AAA GTA AAT CAA AGG AAG GAG TCT GAA TTT GTC ATG CAG GTG ACT GGT TCT AAT
    R   A   K   V   N   Q   R   K   E   S   E   F   V   M   Q   V   T   G   S   N
301
    ATC GAT GAG GGC AAG GCA AGT ATG GAT GTT GAG CAT CTT TAT CTG AAG CTG TAG agg aat
    I   D   E   G   K   A   S   M   D   V   E   H   L   Y   L   K   L   *
361
    att cga gta tag aaa aaa gta aat ttc aag tta aaa ttt gtt gtt ttt tgt atg aat tag
421
    aca aaa aat taa ata aaa ata gga ttt aga aaa aaa aaa aaa aaa aaa a
```

FIG. 1

```
1
  ttg ggt ttt aat tac cca agt ttg agg gta ttc aaa gtc att ATG GCG GAT GTT CGG CCT
                                                          M   A   D   V   R   P
61
  AAG ACG GTT CCA AAA GAG CAG CAC CCT TTT TAC ATC CTC CAC CCC GAG CCT ATT CGA ATC
  K   T   V   P   K   E   Q   H   P   F   Y   I   L   H   P   E   P   I   R   I
121
  TCT CCG CTG CTC CGA TTT GCT CGT TGG TCG GCC CTC GGC CTA GGC ATT GTG TAT GGT TTC
  S   P   L   L   R   F   A   R   W   S   A   L   G   L   G   I   V   Y   G   F
181
  GTC CGT CTT CGT ATG GTC AGC AAA TAC CAC GCG GAC ATC CGC GAA TGG CTG CGT GAG CAA AAG
  V   R   L   R   M   V   S   K   Y   H   A   D   I   R   E   W   L   R   E   Q   K
241
  ACC ATC CAC AAG AAG AAG GAT GCG GAT AAG GAG TCA CTG AGA GTG CTG CGT GAG CAA AAC
  T   I   H   K   K   K   D   A   D   K   E   S   L   R   V   L   R   E   Q   N
301
  GAA TGG ATT ATG AAG ATC ACC GAC ATG AAT TTG GAG GAG GGA AAG TCG CAA TTG GGC GTG
  E   W   I   M   K   I   T   D   M   N   L   E   E   G   K   S   Q   L   G   V
361
  GAG CAT TTG TAC GAT TTG AAA TAG aaa gcg aag aat cgt ctc aca acg aca aat tgc gat
  E   H   L   Y   D   L   K   *
421
  tag gga ttt ctt tgt gtt atc agt cac agt tga cga acc ttt caa ttg ttt tgt ttg gaa
481
  aaa caa tgt tat tgt aga ttt cgt aaa aat aaa gaa
```

FIG. 2

```
1   gcc gcc agt gtg atg gat atc tgc aga att cgc cct ttt taa tta ccc aag ttt gag
61  gtc ATG CCC ATT GGA AAA AAC CCC GCT TTT CAA TAT CAC GTC CCA GAA CCA ATC CCG GTT
     M   P   I   G   K   N   P   A   F   Q   Y   H   V   P   E   P   I   P   V
121 TCT CCA TTG ATC AGA GCA ACC CGT TGG GGA CTT CTT GGT TTG GGT ATC GTA TGG GGT GCT
     S   P   L   I   R   A   T   R   W   G   L   L   G   L   G   I   V   W   G   A
181 ATC CGT TAT CGT CAA ATT TGT GAG AAG CAT GCT GAT ATC CGC GCA TGG GAG CAT GAC CAA
     I   R   Y   R   Q   I   C   E   K   H   A   D   I   R   A   W   E   H   D   Q
241 GAT ACG GAA CTA ACG CTT GAA AAC AAT CGC AAA GCT CGT TTG GCA CTC CGT GAA CAA CTT
     D   T   E   L   T   L   E   N   N   R   K   A   R   L   A   L   R   E   Q   L
301 ATC GTC TTA TGG AAA CAA ATC GGT CTG CCA TTC AAC GAA GGT GTC GCC TCC TTC AAG GCC
     I   V   L   W   K   Q   I   G   L   P   F   N   E   G   V   A   S   F   K   A
361 AAC GAT CTT TTC CGT GAC GAA TAG gac ttt ttt aaa acc aaa aat agc ata ttt agt tta
     N   D   L   F   R   D   E   *
421 tat ttg ttt att ttt aaa aaa ctt gag ctg tct ata aaa atg tct tag atc aaa aaa aaa
481 aaa aaa aaa
```

FIG. 3

SEQUENCE LISTING

```
<160> NUMBER OF SEQ ID NOS: 14

<210> SEQ ID NO 1
<211> LENGTH: 466
<212> TYPE: DNA
<213> ORGANISM: Meloidogyne javanica
<220> FEATURE:
<221> NAME/KEY: CDS
<222> LOCATION: (40)...(351)

<400> SEQUENCE: 1
gtttaattac ccaagtttga gataaaattt atttaaaaa atg tca aag ccg cat          54
                                            Met Ser Lys Pro His
                                             1               5 ccg acc gat ata att ctt cct gaa cca atc cag gtt tca ccg tta att      102
Pro Thr Asp Ile Ile Leu Pro Glu Pro Ile Gln Val Ser Pro Leu Ile
             10                  15                  20 cgt ttt gct cgt tgg act gct ctt ggt gcg gga ata att tat ggc tat      150
Arg Phe Ala Arg Trp Thr Ala Leu Gly Ala Gly Ile Ile Tyr Gly Tyr
         25                  30                  35 gtt cgt ttc cat caa att gct cgt ggt cat gca ctt att cgt gaa tgg      198
Val Arg Phe His Gln Ile Ala Arg Gly His Ala Leu Ile Arg Glu Trp
     40                  45                  50 gag gct gat aaa ttt atc cat aaa gtt gaa cag gag cat gag aga gct      246
Glu Ala Asp Lys Phe Ile His Lys Val Glu Gln Glu His Glu Arg Ala
 55                  60                  65 aaa gta aat caa agg aag gag tct gaa ttt gtc atg cag gtg act ggt      294
Lys Val Asn Gln Arg Lys Glu Ser Glu Phe Val Met Gln Val Thr Gly
 70                  75                  80                  85 tct aat atc gat gag ggc aag gca agt atg gat gtt gag cat ctt tat      342
Ser Asn Ile Asp Glu Gly Lys Ala Ser Met Asp Val Glu His Leu Tyr
                 90                  95                 100 ctg aag ctg tagaggaata ttcgagtata gaaaaagta aatttcaagt                391
Leu Lys Leu
```

Leu Lys Leu

```
taaaatttgt tgtttttgt atgaattaga caaaaaatta aataaaaata ggatttagaa     451
aaaaaaaaaa aaaaa                                                      466
```

<210> SEQ ID NO 2
<211> LENGTH: 516
<212> TYPE: DNA
<213> ORGANISM: Heterodera glycines
<220> FEATURE:
<221> NAME/KEY: CDS
<222> LOCATION: (43)...(381)

<400> SEQUENCE: 2

```
ttgggtttta attacccaag tttgagggta ttcaaagtca tt atg gcg gat gtt         54
                                              Met Ala Asp Val
                                                1 cgg cct aag acg gtt cca aaa gag cag cac cct ttt tac atc ctc cac       102
Arg Pro Lys Thr Val Pro Lys Glu Gln His Pro Phe Tyr Ile Leu His
  5              10                 15                  20 ccc gag cct att cga atc tct ccg ctg ctc cga ttt gct cgt tgg tcg       150
Pro Glu Pro Ile Arg Ile Ser Pro Leu Leu Arg Phe Ala Arg Trp Ser
         25                  30                  35 gcc ctc ggc cta ggc att gtg tat ggt ttc gtc cgt ctt cgt atg gtc       198
Ala Leu Gly Leu Gly Ile Val Tyr Gly Phe Val Arg Leu Arg Met Val
 40                  45                  50 agc aaa tac cac gcg gac atc cgc gaa tgg gaa gtg caa aag acc atc       246
Ser Lys Tyr His Ala Asp Ile Arg Glu Trp Glu Val Gln Lys Thr Ile
     55                  60                  65 cac aag aag gat gcg gat aag aag gag tca ctg aga gtg ctg cgt gag       294
His Lys Lys Asp Ala Asp Lys Lys Glu Ser Leu Arg Val Leu Arg Glu
 70                  75                  80 caa aac gaa tgg att atg aag atc acc gac atg aat ttg gag gag gga       342
Gln Asn Glu Trp Ile Met Lys Ile Thr Asp Met Asn Leu Glu Glu Gly
 85                  90                  95                 100 aag tcg caa ttg ggc gtg gag cat ttg tac gat ttg aaa tagaaagcga       391
Lys Ser Gln Leu Gly Val Glu His Leu Tyr Asp Leu Lys
            105                 110 agaatcgtct cacaacgaca aattgcgatt agggatttct ttgtgttatc agtcacagtt   451
gacgaacctt tcaattgttt tgtttggaaa acaatgtta tgtagatttt cgtaaaaata    511
aagaa                                                              516
```

<210> SEQ ID NO 3
<211> LENGTH: 489
<212> TYPE: DNA
<213> ORGANISM: Zeldia punctata
<220> FEATURE:
<221> NAME/KEY: CDS
<222> LOCATION: (64)...(381)

<400> SEQUENCE: 3

```
gccgccgcca gtgtgatgga tatctgcaga attcgcccctt tttaattacc caagtttgag    60 gtc atg ccc att gga aaa aac ccc gct ttt caa tat cac gtc cca gaa       108
    Met Pro Ile Gly Lys Asn Pro Ala Phe Gln Tyr His Val Pro Glu
      1               5                  10                  15 cca atc ccg gtt tct cca ttg atc aga gca acc cgt tgg gga ctt ctt       156
Pro Ile Pro Val Ser Pro Leu Ile Arg Ala Thr Arg Trp Gly Leu Leu
             20                  25                  30 ggt ttg ggt atc gta tgg ggt gct atc cgt tat cgt caa att tgt gag       204
Gly Leu Gly Ile Val Trp Gly Ala Ile Arg Tyr Arg Gln Ile Cys Glu
         35                  40                  45
```

```
aag cat gct gat atc cgc gca tgg gag cat gac caa gat acg gaa cta      252
Lys His Ala Asp Ile Arg Ala Trp Glu His Asp Gln Asp Thr Glu Leu
        50                  55                  60 acg ctt gaa aac aat cgc aaa gct cgt ttg gca ctc cgt gaa caa ctt      300
Thr Leu Glu Asn Asn Arg Lys Ala Arg Leu Ala Leu Arg Glu Gln Leu
65                  70                  75 atc gtc tta tgg aaa caa atc ggt ctg cca ttc aac gaa ggt gtc gcc      348
Ile Val Leu Trp Lys Gln Ile Gly Leu Pro Phe Asn Glu Gly Val Ala
    80                  85                  90                  95 tcc ttc aag gcc aac gat ctt ttc cgt gac gaa taggactttt ttaaaaccaa    401
Ser Phe Lys Ala Asn Asp Leu Phe Arg Asp Glu
                100                 105 aaatagcata tttagtttat atttgtttat ttttaaaaaa cttgagctgt ctataaaaat    461
gtcttagatc aaaaaaaaaa aaaaaaa                                        489

<210> SEQ ID NO 4
<211> LENGTH: 104
<212> TYPE: PRT
<213> ORGANISM: Meloidogyne javanica

<400> SEQUENCE: 4

Met Ser Lys Pro His Pro Thr Asp Ile Ile Leu Pro Glu Pro Ile Gln
1               5                   10                  15

Val Ser Pro Leu Ile Arg Phe Ala Arg Trp Thr Ala Leu Gly Ala Gly
                20                  25                  30

Ile Ile Tyr Gly Tyr Val Arg Phe His Gln Ile Ala Arg Gly His Ala
            35                  40                  45

Leu Ile Arg Glu Trp Glu Ala Asp Lys Phe Ile His Lys Val Glu Gln
        50                  55                  60

Glu His Glu Arg Ala Lys Val Asn Gln Arg Lys Glu Ser Glu Phe Val
65                  70                  75                  80

Met Gln Val Thr Gly Ser Asn Ile Asp Glu Gly Lys Ala Ser Met Asp
                85                  90                  95

Val Glu His Leu Tyr Leu Lys Leu
            100

<210> SEQ ID NO 5
<211> LENGTH: 113
<212> TYPE: PRT
<213> ORGANISM: Heterodera glycines

<400> SEQUENCE: 5

Met Ala Asp Val Arg Pro Lys Thr Val Pro Lys Glu Gln His Pro Phe
1               5                   10                  15

Tyr Ile Leu His Pro Glu Pro Ile Arg Ile Ser Pro Leu Leu Arg Phe
                20                  25                  30

Ala Arg Trp Ser Ala Leu Gly Leu Gly Ile Val Tyr Gly Phe Val Arg
            35                  40                  45

Leu Arg Met Val Ser Lys Tyr His Ala Asp Ile Arg Glu Trp Glu Val
        50                  55                  60

Gln Lys Thr Ile His Lys Lys Asp Ala Asp Lys Lys Glu Ser Leu Arg
65                  70                  75                  80

Val Leu Arg Glu Gln Asn Glu Trp Ile Met Lys Ile Thr Asp Met Asn
                85                  90                  95

Leu Glu Glu Gly Lys Ser Gln Leu Gly Val Glu His Leu Tyr Asp Leu
            100                 105                 110
```

Lys

<210> SEQ ID NO 6
<211> LENGTH: 106
<212> TYPE: PRT
<213> ORGANISM: Zeldia punctata

<400> SEQUENCE: 6

```
Met Pro Ile Gly Lys Asn Pro Ala Phe Gln Tyr His Val Pro Glu Pro
 1               5                  10                  15

Ile Pro Val Ser Pro Leu Ile Arg Ala Thr Arg Trp Gly Leu Leu Gly
            20                  25                  30

Leu Gly Ile Val Trp Gly Ala Ile Arg Tyr Arg Gln Ile Cys Glu Lys
        35                  40                  45

His Ala Asp Ile Arg Ala Trp Glu His Asp Gln Asp Thr Glu Leu Thr
    50                  55                  60

Leu Glu Asn Asn Arg Lys Ala Arg Leu Ala Leu Arg Glu Gln Leu Ile
65                  70                  75                  80

Val Leu Trp Lys Gln Ile Gly Leu Pro Phe Asn Glu Gly Val Ala Ser
                85                  90                  95

Phe Lys Ala Asn Asp Leu Phe Arg Asp Glu
            100                 105
```

<210> SEQ ID NO 7
<211> LENGTH: 312
<212> TYPE: DNA
<213> ORGANISM: Meloidogyne javanica

<400> SEQUENCE: 7

```
atgtcaaagc cgcatccgac cgatataatt cttcctgaac caatccaggt ttcaccgtta    60
attcgttttg ctcgttggac tgctcttggt gcgggaataa tttatggcta tgttcgtttc   120
catcaaattg ctcgtggtca tgcacttatt cgtgaatggg aggctgataa atttatccat   180
aaagttgaac aggagcatga gagagctaaa gtaaatcaaa ggaaggagtc tgaatttgtc   240
atgcaggtga ctggttctaa tatcgatgag ggcaaggcaa gtatggatgt tgagcatctt   300
tatctgaagc tg                                                       312
```

<210> SEQ ID NO 8
<211> LENGTH: 339
<212> TYPE: DNA
<213> ORGANISM: Heterodera glycines

<400> SEQUENCE: 8

```
atggcggatg ttcggcctaa gacggttcca aaagagcagc accctttta catcctccac     60 cccgagccta ttcgaatctc tccgctgctc cgatttgctc gttggtcggc cctcggccta   120
ggcattgtgt atggtttcgt ccgtcttcgt atggtcagca ataccacgc ggacatccgc    180 gaatgggaag tgcaaaagac catccacaag aaggatgcgg ataagaagga gtcactgaga   240
gtgctgcgtg agcaaaacga atggattatg aagatcaccg acatgaattt ggaggaggga   300
aagtcgcaat gggcgtgga gcatttgtac gatttgaaa                           339
```

<210> SEQ ID NO 9
<211> LENGTH: 318
<212> TYPE: DNA
<213> ORGANISM: Zeldia punctata

<400> SEQUENCE: 9

```
atgcccattg gaaaaaaccc cgcttttcaa tatcacgtcc cagaaccaat cccggtttct    60
ccattgatca gagcaacccg ttggggactt cttggtttgg gtatcgtatg gggtgctatc   120
cgttatcgtc aaatttgtga agcatgct gatatccgcg catgggagca tgaccaagat    180
acggaactaa cgcttgaaaa caatcgcaaa gctcgtttgg cactccgtga acaacttatc   240
gtcttatgga aacaaatcgg tctgccattc aacgaaggtg tcgcctcctt caaggccaac   300
gatcttttcc gtgacgaa                                                 318

<210> SEQ ID NO 10
<211> LENGTH: 107
<212> TYPE: PRT
<213> ORGANISM: Caenorhabidits elegans

<400> SEQUENCE: 10

Met Ser Ala Pro Leu Lys His Pro Asn Ala Val Val Leu Gln Pro Pro
 1               5                  10                  15

Thr Val Thr Ile Ser Pro Leu Ile Arg Phe Gly Arg Tyr Ala Ala Leu
            20                  25                  30

Ser Leu Gly Val Val Tyr Gly Phe Phe Arg Leu Arg Gln Ile Arg Glu
        35                  40                  45

Tyr His Ala Asp Ile Arg Glu Trp Asp His Glu Lys Ala Val Ala Ala
    50                  55                  60

Ala Glu Glu Ala Ala Lys Lys Lys Trp Leu Ala Lys Asp Glu Met
65                  70                  75                  80

Arg Tyr Leu Met Gln Val Val Asn Ile Pro Phe Glu Glu Gly Val Lys
                85                  90                  95

Gln Phe Gly Val Ala Asp Leu Tyr Lys Glu Asp
            100                 105

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
gtaatacgac tcactatagg ggc                                            23

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
aattaaccct cactaaaggg                                                20

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
gggtttaatt acccaagttt ga                                             22

<210> SEQ ID NO 14
```

```
<211> LENGTH: 50
<212> TYPE: DNA
<213> ORGANISM: Artificial Sequence
<220> FEATURE:
<223> OTHER INFORMATION: primer

<400> SEQUENCE: 14
gagagagaga gagagagaga actagtctcg agtttttttt tttttttttt            50
```

NEMATODE ATP SYNTHASE SUBUNIT E POLYPEPTIDE

RELATED APPLICATION INFORMATION

This application is a divisional of U.S. application Ser. No. 11/091,969, filed Mar. 28, 2005, now abandoned, which is a divisional of U.S. application Ser. No. 10/160,362, filed May 30, 2002, now U.S. Pat. No. 6,903,190, which claims priority to provisional application Ser. No. 60/294,777, filed May 31, 2001, all of which are hereby incorporated by reference.

BACKGROUND

Nematodes (derived from the Greek word for thread) are active, flexible, elongate, organisms that live on moist surfaces or in liquid environments, including films of water within soil and moist tissues within other organisms. While only 20,000 species of nematode have been identified, it is estimated that 40,000 to 10 million actually exist. Some species of nematodes have evolved as very successful parasites of both plants and animals and are responsible for significant economic losses in agriculture and livestock and for morbidity and mortality in humans (Whitehead (1998) *Plant Nematode Control.*, CAB International, New York).

Nematode parasites of plants can inhabit all parts of plants, including roots, developing flower buds, leaves, and stems. Plant parasites are classified on the basis of their feeding habits into the broad categories: migratory ectoparasites, migratory endoparasites, and sedentary endoparasites. Sedentary endoparasites, which include the root knot nematodes (*Meloidogyne*) and cyst nematodes (*Globodera* and *Heterodera*) induce feeding sites and establish long-term infections within roots that are often very damaging to crops (Whitehead, supra). It is estimated that parasitic nematodes cost the horticulture and agriculture industries in excess of $78 billion worldwide a year, based on an estimated average 12% annual loss spread across all major crops. For example, it is estimated that nematodes cause soybean losses of approximately $3.2 billion annually worldwide (Barker et al. (1994) *Plant and Soil Nematodes: Societal Impact and Focus for the Future*. The Committee on National Needs and Priorities in Nematology. Cooperative State Research Service, US Department of Agriculture and Society of Nematologists). Several factors make the need for safe and effective nematode controls urgent. Continuing population growth, famines, and environmental degradation have heightened concern for the sustainability of agriculture, and new government regulations may prevent or severely restrict the use of many available agricultural anthelmintic agents.

The situation is particularly dire for high value crops such as strawberries and tomatoes where chemicals have been used extensively to control soil pests. The soil fumigant methyl bromide has been used effectively to reduce nematode infestations in a variety of these specialty crops. It is however regulated under the U.N. Montreal Protocol as an ozone-depleting substance and is scheduled for elimination in 2005 in the US (Carter (2001) *Califonia Agriculture*, 55(3):2). It is expected that strawberry and other commodity crop industries will be significantly impacted if a suitable replacement for methyl bromide is not found. Presently there are a very small array of chemicals available to control nematodes and they are frequently inadequate, unsuitable, or too costly for some crops or soils (Becker (1999) *Agricultural Research Magazine* 47(3):22-24; U.S. Pat. No. 6,048,714). The few available broad-spectrum nematicides such as Telone (a mixture of 1,3-dichloropropene and chloropicrin) have significant restrictions on their use because of toxicological concerns (Carter (2001) *California Agriculture* 55(3):12-18).

Fatty acids are a class of natural compounds that have been investigated as alternatives to the toxic, non-specific organophosphate, carbamate and fumigant pesticides (Stadler et al. (1994) *Planta Medica* 60(2):128-132; U.S. Pat. Nos. 5,192, 546; 5,346,698; 5,674,897; 5,698,592; 6,124,359). It has been suggested that fatty acids derive their pesticidal effects by adversely interfering with the nematode cuticle or hypodermis via a detergent (solubilization) effect, or through direct interaction of the fatty acids and the lipophilic regions of target plasma membranes (Davis et al. (1997) *Journal of Nematology* 29(4S):677-684). In view of this general mode of action it is not surprising that fatty acids are used in a variety of pesticidal applications including as herbicides (e.g., SCYTHE by Dow Agrosciences is the C9 saturated fatty acid pelargonic acid), as bactericides and fungicides (U.S. Pat. Nos. 4,771,571; 5,246,716) and as insecticides (e.g., SAFER INSECTICIDAL SOAP by Safer, Inc.).

The phytotoxicity of fatty acids has been a major constraint on their general use in agricultural applications (U.S. Pat. No. 5,093,124) and the mitigation of these undesirable effects while preserving pesticidal activity is a major area of research. The esterification of fatty acids can significantly decrease their phytotoxicity (U.S. Pat. Nos. 5,674,897; 5,698, 592; 6,124,359). Such modifications can however lead to dramatic loss of nematicidal activity as is seen for linoleic, linolenic and oleic acid (Stadler et al. (1994) *Planta Medica* 60(2):128-132) and it may be impossible to completely decouple the phytotoxicity and nematicidal activity of pesticidal fatty acids because of their non-specific mode of action. Perhaps not surprisingly, the nematicidal fatty acid pelargonic acid methyl ester (U.S. Pat. Nos. 5,674,897; 5,698,592; 6,124,359) shows a relatively small "therapeutic window" between the onset of pesticidal activity and the observation of significant phytotoxicity (Davis et al. (1997) *J. Nematol.* 29(4S):677-684). This is the expected result if both the phytotoxicity and the nematicidial activity derive from the non-specific disruption of plasma membrane integrity. Similarly the rapid onset of pesticidal activity seen with many nematicidal fatty acids at therapeutic concentrations (U.S. Pat. Nos. 5,674,897; 5,698,592; 6,124,359) suggests a non-specific mechanism of action, possibly related to the disruption of membranes, action potentials and neuronal activity.

Ricinoleic acid, the major component of castor oil, provides another example of the unexpected effects esterification can have on fatty acid activity. Ricinoleic acid has been shown to have an inhibitory effect on water and electrolyte absorption using everted hamster jejunal and ileal segments (Gaginella et al. (1975) *J. Pharmacol. Exp. Ther.* 195(2):355-61) and to be cytotoxic to isolated intestinal epithelial cells (Gaginella et al. (1977) *J. Pharmacol. Exp. Ther.* 201(1):259-66). These features are likely the source of the laxative properties of castor oil which is given as a purgative in humans and livestock. In fact, castor oil is a component of some deworming protocols because of its laxative properties. In contrast, the methyl ester of ricinoleic acid is ineffective at suppressing water absorption in the hamster model (Gaginella et al. (1975) *J. Pharmacol. Exp. Ther.* 195(2):355-61).

The macrocyclic lactones (e.g., avermectins and milbemycins) and delta-toxins from *Bacillus thuringiensis* (Bt) are chemicals that, in principle, provide excellent specificity and efficacy and should allow environmentally safe control of plant parasitic nematodes. Unfortunately, in practice, these two approaches have proven less effective for agricultural applications against root pathogens. Although certain avermectins show exquisite activity against plant parasitic nematodes these chemicals are hampered by poor bioavailability due to their light sensitivity, degradation by soil microorganisms and tight binding to soil particles (Lasota & Dybas (1990) *Acta Leiden* 59(1-2):217-225; Wright & Perry (1998) Musculature and Neurobiology. In: The Physiology and Biochemistry of Free-Living and Plant-parasitic Nematodes (eds R. N. Perry & D. J. Wright), CAB International 1998). Consequently despite years of research and extensive use against animal parasitic nematodes, mites and insects (plant and animal applications), macrocyclic lactones (e.g., avermectins and milbemycins) have never been commercially developed to control plant parasitic nematodes in the soil.

Bt delta toxins must be ingested to affect their target organ the brush border of midgut epithelial cells (Marroquin et al. (2000) *Genetics* 155(4): 1693-1699). Consequently they are not anticipated to be effective against the dispersal, non-feeding, juvenile stages of plant parasitic nematodes in the field. These juvenile stages only commence feeding when a susceptible host has been infected, thus to be effective nematicides may need to penetrate the cuticle. In addition, soil mobility of a relatively large 65-130 kDa protein—the size of typical Bt delta toxins—is expected to be poor and delivery in planta is likely to be constrained by the exclusion of large particles by the feeding tube of certain plant parasitic nematodes such as *Heterodera* (Atkinson et al. (1998) Engineering resistance to plant-parasitic nematodes. In: The Physiology and Biochemistry of Free-Living and Plant-parasitic Nematodes (eds R. N. Perry & D. J. Wright), CAB International 1998).

Many plant species are known to be highly resistant to nematodes. The most well documented of these include marigolds (*Tagetes* spp.), rattlebox (*Crotalaria spectabilis*), chrysanthemums (*Chrysanthemum* spp.), castor bean (*Ricinus communis*), margosa (*Azardiracta indica*), and many members of the family Asteraceae (family Compositae) (Hackney & Dickerson (1975) *J. Nematol.* 7(1):84-90). The active principle(s) for this nematicidal activity has not been discovered in all of these examples and no plant-derived products are sold commercially for control of nematodes. In the case of the Asteraceae, the photodynamic compound alpha-terthienyl has been shown to account for the strong nematicidal activity of the roots. Castor beans are plowed under as a green manure before a seed crop is set. However, a significant drawback of the castor plant is that the seed contains toxic compounds (such as ricin) that can kill humans, pets, and livestock and is also highly allergenic.

There remains an urgent need to develop environmentally safe, target-specific ways of controlling plant parasitic nematodes. In the specialty crop markets, economic hardship resulting from nematode infestation is highest in strawberries, bananas, and other high value vegetables and fruits. In the high-acreage crop markets, nematode damage is greatest in soybeans and cotton. There are however, dozens of additional crops that suffer from nematode infestation including potato, pepper, onion, citrus, coffee, sugarcane, greenhouse ornamentals and golf course turf grasses.

Nematode parasites of vertebrates (e.g., humans, livestock and companion animals) include gut roundworms, hookworms, pinworms, whipworms, and filarial worms. They can be transmitted in a variety of ways, including by water contamination, skin penetration, biting insects, or by ingestion of contaminated food.

In domesticated animals, nematode control or "de-worming" is essential to the economic viability of livestock producers and is a necessary part of veterinary care of companion animals. Parasitic nematodes cause mortality in animals (e.g., heartworm in dogs and cats) and morbidity as a result of the parasites' inhibiting the ability of the infected animal to absorb nutrients. The parasite-induced nutrient deficiency results in diseased livestock and companion animals (i.e., pets), as well as in stunted growth. For instance, in cattle and dairy herds, a single untreated infection with the brown stomach worm can permanently stunt an animal's ability to effectively convert feed into muscle mass or milk.

Two factors contribute to the need for novel anthelmintics and vaccines for control of parasitic nematodes of animals. First, some of the more prevalent species of parasitic nematodes of livestock are building resistance to the anthelmintic drugs available currently, meaning that these products will eventually lose their efficacy. These developments are not surprising because few effective anthelmintic drugs are available and most have been used continuously. Presently a number of parasitic species has developed resistance to most of the anthelmintics (Geents et al. (1997) Parasitology Today 13:149-151; Prichard (1994) Veterinary Parasitology 54:259-268). The fact that many of the anthelmintic drugs have similar modes of action complicates matters, as the loss of sensitivity of the parasite to one drug is often accompanied by side resistance—that is, resistance to other drugs in the same class (Sangster & Gill (1999) Parasitology Today 15(4):141-146). Secondly, there are some issues with toxicity for the major compounds currently available.

Human infections by nematodes result in significant mortality and morbidity, especially in tropical regions of Africa, Asia, and the Americas. The World Health Organization estimates 2.9 billion people are infected with parasitic nematodes. While mortality is rare in proportion to total infections (180,000 deaths annually), morbidity is tremendous and rivals tuberculosis and malaria in disability adjusted life year measurements. Examples of human parasitic nematodes include hookworm, filarial worms, and pinworms. Hookworm is the major cause of anemia in millions of children, resulting in growth retardation and impaired cognitive development. Filarial worm species invade the lymphatics, resulting in permanently swollen and deformed limbs (elephantiasis) and invade the eyes causing African Riverblindness. *Ascaris lumbricoides*, the large gut roundworm infects more than one billion people worldwide and causes malnutrition and obstructive bowl disease. In developed countries, pinworms are common and often transmitted through children in daycare.

Even in asymptomatic parasitic infections, nematodes can still deprive the host of valuable nutrients and increase the ability of other organisms to establish secondary infections. In some cases, infections can cause debilitating illnesses and can result in anemia, diarrhea, dehydration, loss of appetite, or death.

While public health measures have nearly eliminated one tropical nematode (the water-borne Guinea worm), cases of other worm infections have actually increased in recent decades. In these cases, drug intervention provided through foreign donations or purchased by those who can afford it remains the major means of control. Because of the high rates of reinfection after drug therapy, vaccines remain the best hope for worm control in humans. There are currently no vaccines available.

Until safe and effective vaccines are discovered to prevent parasitic nematode infections, anthelmintic drugs will continue to be used to control and treat nematode parasitic infections in both humans and domestic animals. Finding effective compounds against parasitic nematodes has been complicated by the fact that the parasites have not been amenable to culturing in the laboratory. Parasitic nematodes are often obligate parasites (i.e., they can only survive in their respective hosts, such as in plants, animals, and/or humans) with slow generation times. Thus, they are difficult to grow under artificial conditions, making genetic and molecular experimentation difficult or impossible. To circumvent these limitations, scientists have used *Caenorhabidits elegans* as a model system for parasitic nematode discovery efforts.

*C. elegans* is a small free-living bacteriovorous nematode that for many years has served as an important model system for multicellular animals (Burglin (1998) *Int. J. Parasitol.* 28(3): 395-411). The genome of *C. elegans* has been completely sequenced and the nematode shares many general developmental and basic cellular processes with vertebrates (Ruvkin et al. (1998) *Science* 282: 2033-41). This, together with its short generation time and ease of culturing, has made it a model system of choice for higher eukaryotes (Aboobaker et al. (2000) *Ann. Med.* 32: 23-30).

Although *C. elegans* serves as a good model system for vertebrates, it is an even better model for study of parasitic nematodes, as *C. elegans* and other nematodes share unique biological processes not found in vertebrates. For example, unlike vertebrates, nematodes produce and use chitin, have gap junctions comprised of innexin rather than connexin and contain glutamate-gated chloride channels rather than glycine-gated chloride channels (Bargmann (1998) *Science* 282: 2028-33). The latter property is of particular relevance given that the avermectin class of drugs is thought to act at glutamate-gated chloride receptors and is highly selective for invertebrates (Martin (1997) *Vet. J.* 154:11-34).

A subset of the genes involved in nematode specific processes will be conserved in nematodes and absent or significantly diverged from homologues in other phyla. In other words, it is expected that at least some of the genes associated with functions unique to nematodes will have restricted phylogenetic distributions. The completion of the *C. elegans* genome project and the growing database of expressed sequence tags (ESTs) from numerous nematodes facilitate identification of these "nematode specific" genes. In addition, conserved genes involved in nematode-specific processes are expected to retain the same or very similar functions in different nematodes. This functional equivalence has been demonstrated in some cases by transforming *C. elegans* with homologous genes from other nematodes (Kwa et al. (1995) *J. Mol. Biol.* 246:500-10; Redmond et al. (2001) *Mol. Biochem. Parasitol.* 112:125-131). This sort of data transfer has been shown in cross phyla comparisons for conserved genes and is expected to be more robust among species within a phylum. Consequently, *C. elegans* and other free-living nematode species are likely excellent surrogates for parasitic nematodes with respect to conserved nematode processes.

Many expressed genes in *C. elegans* and certain genes in other free-living nematodes can be "knocked out" genetically by a process referred to as RNA interference (RNAi), a technique that provides a powerful experimental tool for the study of gene function in nematodes (Fire et al. (1998) *Nature* 391:806-811; Montgomery et al. (1998) *Proc. Natl. Acad. Sci. USA* 95(26):15502-15507). Treatment of a nematode with double-stranded RNA of a selected gene can destroy expressed sequences corresponding to the selected gene thus reducing expression of the corresponding protein. By preventing the translation of specific proteins, their functional significance and essentiality to the nematode can be assessed. Determination of essential genes and their corresponding proteins using *C. elegans* as a model system will assist in the rational design of anti-parasitic nematode control products.

SUMMARY

The invention features nucleic acid molecules encoding *Meloidogyne javanica*, *Heterodera glycines*, and *Zeldia punctata* ATP synthase subunit E and other nematode ATP synthase subunit E-like proteins. *M. javanica* is a Root Knot Nematode that causes substantial damage to several crops, including cotton, tobacco, pepper, and tomato. *H. glycines*, referred to as Soybean Cyst Nematode, is a major pest of soybean. *Z. punctata* is free-living nematode that serves as a model for parasitic nematodes. The ATP synthase subunit E-like nucleic acids and polypeptides of the invention allow for the identification of a nematode species, and for the identification of compounds that bind to or alter the activity of ATP synthase subunit E-like polypeptides. Such compounds may provide a means for combating diseases and infestations caused by nematodes, particularly those caused by *M. javanica* (e.g., in tobacco, cotton, pepper, or tomato plants) and by *H. glycines*, (e.g., in soybean).

The invention is based, in part, on the identification of a cDNA encoding *M. javanica* ATP synthase subunit E (SEQ ID NO: 1). This 466 nucleotide cDNA has a 312 nucleotide open reading frame (SEQ ID NO: 7) encoding a 104 amino acid polypeptide (SEQ ID NO: 4).

The invention is also based, in part, on the identification of a cDNA encoding *H. glycines* ATP synthase subunit E (SEQ ID NO: 2). This 516 nucleotide cDNA has a 339 nucleotide open reading frame (SEQ ID NO: 8) encoding a 113 amino acid polypeptide (SEQ ID NO: 5).

The invention is also based, in part, on the identification of a cDNA encoding *Z. punctata* ATP synthase subunit E (SEQ ID NO: 3). This 489 nucleotide cDNA has a 318 nucleotide open reading frame (SEQ ID NO: 9) encoding a 106 amino acid polypeptide (SEQ ID NO: 6).

In one aspect, the invention features novel nematode ATP synthase subunit E-like polypeptides. Such polypeptides include purified polypeptides having the amino acid sequences set forth in SEQ ID NO: 4, 5, and/or 6. Also included are polypeptides having an amino acid sequence that is at least about 60%, 70%, 75%, 80%, 85%, 90%, 95%, or 98% identical to SEQ ID NO: 4, 5, and/or 6. The invention includes polypeptides comprising, consisting of, or consisting essentially of such polypeptides. The invention also features such polypeptides linked, e.g., by a peptide bond to at least one heterologous polypeptide to form a fusion protein. The ATP synthase subunit E-like polypeptide can be flanked by heterologous polypeptides or by one or more heterologous amino acids. The purified polypeptides can be encoded by a nematode gene, e.g., a nematode gene other than *C. elegans*. For example, the purified polypeptide has a sequence other than SEQ ID NO: 10 (*C. elegans* ATP synthase subunit E). The purified polypeptides can further include a heterologous amino acid sequence, e.g., an amino-terminal or carboxy-terminal amino acids (or both) that are not part of the naturally occurring sequence. Also featured are purified polypeptide fragments of the aforementioned ATP synthase subunit E-like polypeptides, e.g., a fragment of at least about 20, 30, 40, 50, 75, 85, 104, 106, 113 amino acids. Non-limiting examples of such fragments include: fragments from about amino acid 1 to 50, 1 to 75, 1 to 89, 1 to 91, 1 to 99, 1 to 100, 1 to 125, 51 to 113, 93 to 104, 99 to 113, and 93 to 106 of SEQ ID NO: 4, 5, and/or 6. The polypeptide or fragment thereof can be modified, e.g., processed, truncated, modified (e.g. by glycosylation, phosphorylation, acetylation, myristylation, prenylation, palmitoylation, amidation, addition of glycerophosphatidyl inositol), or any combination of the above.

Certain ATP synthase subunit E-like polypeptides comprise a sequence of 104, 106, 113, 125, 150 amino acids or fewer.

In another aspect, the invention features novel isolated nucleic acid molecules encoding nematode ATP synthase subunit E-like polypeptides. Such isolated nucleic acid molecules include nucleic acids having the nucleotide sequence set forth in SEQ ID NO: 1, 2, and/or 3 or SEQ ID NO: 7, 8, and/or 9. Also included are isolated nucleic acid molecules having the same sequence as or encoding the same polypeptide as a nematode ATP synthase subunit E-like gene (other than *C. elegans* ATP synthase subunit E-like genes).

Also featured are: 1) isolated nucleic acid molecules (e.g., nucleic acid probes) having a strand that hybridizes under low stringency conditions to a single stranded probe of the sequences of SEQ ID NO: 1, 2, and/or 3 or their complements and, optionally, encodes polypeptides of between 104 and 106 or 113 amino acids; 2) isolated nucleic acid molecules having a strand that hybridizes under high stringency conditions to a single stranded probe of the sequence of SEQ ID NO: 1, 2, and/or 3 or their complements and, optionally, encodes polypeptides of between 104 and 106 or 113 amino acids; 3) isolated nucleic acid fragments of an ATP synthase subunit E-like nucleic acid molecule, e.g., a fragment of SEQ ID NO: 1, 2, and/or 3 that is about 280, 415, 420, 440, and 500 or more nucleotides in length or ranges between such lengths; and 4) oligonucleotides that are complementary to an ATP synthase subunit E-like nucleic acid molecule or an ATP synthase subunit E-like nucleic acid complement, e.g., an oligonucleotide of about 10, 15, 18, 20, 22, 24, 28, 30, 35, 40, 50, 60, 70, 80, or more nucleotides in length. Exemplary oligonucleotides are oligonucleotides which anneal to a site located between nucleotides about 1 to 24, 1 to 48, 1 to 60, 1 to 120, 24 to 48, 24 to 60, 49 to 60, 61 to 180, 381 to 420, 421 to 480, 451 to 466, 451 to 489, and 451 to 516 of SEQ ID NO: 1, 2, and/or 3. Nucleic acid fragments include the following non-limiting examples: nucleotides about 1 to 200, 100 to 300, 200 to 400, 300 to 500, 300 to 466, 300 to 516, and 300 to 489 of SEQ ID NO: 1, 2, and/or 3. Also within the invention are nucleic acid molecules that hybridize under stringent conditions to nucleic acid molecule comprising SEQ ID NO: 1, 2 or 3 and comprise 3,000, 2,000, 1,000 or fewer nucleotides. The isolated nucleic acid can further include a heterologous promoter operably linked to the ATP synthase subunit E-like nucleic acid molecule.

A molecule featured herein can be from a nematode of the class *Araeolaimida, Ascaridida, Chromadorida, Desmodorida, Diplogasterida, Monhysterida, Mononchida, Oxyurida, Rhigonematida, Spirurida, Enoplia, Desmoscolecidae, Rhabditida,* or *Tylenchida*. Alternatively, the molecule can be from a species of the class *Rhabditida*, particularly a species other than *C. elegans*.

In another aspect, the invention features a vector, e.g., a vector containing an aforementioned nucleic acid. The vector can further include one or more regulatory elements, e.g., a heterologous promoter. The regulatory elements can be operably linked to the ATP synthase subunit E-like nucleic acid molecules in order to express an ATP synthase subunit E-like nucleic acid molecule. In yet another aspect, the invention features a transgenic cell or transgenic organism having in its genome a transgene containing an aforementioned ATP synthase subunit E-like nucleic acid molecule and a heterologous nucleic acid, e.g., a heterologous promoter.

In still another aspect, the invention features an antibody, e.g., an antibody, antibody fragment, or derivative thereof that binds specifically to an aforementioned polypeptide. Such antibodies can be polyclonal or monoclonal antibodies. The antibodies can be modified, e.g., humanized, rearranged as a single-chain, or CDR-grafted. The antibodies may be directed against a fragment, a peptide, or a discontinuous epitope from an ATP synthase subunit E-like polypeptide.

In another aspect, the invention features a method of screening for a compound that binds to a nematode ATP synthase subunit E-like polypeptide, e.g., an aforementioned polypeptide. The method includes providing the nematode polypeptide; contacting a test compound to the polypeptide; and detecting binding of the test compound to the nematode polypeptide. In one embodiment, the method further includes contacting the test compound to a mammalian ATP synthase subunit E-like polypeptide; and detecting binding of the test compound to the mammalian ATP synthase subunit E-like polypeptide. A test compound that binds the nematode ATP synthase subunit E-like polypeptide with at least 2-fold, 5-fold, 10-fold, 20-fold, 50-fold, or 100-fold affinity greater relative to its affinity for the mammalian (e.g., a human) ATP synthase subunit E-like polypeptide can be identified.

The invention also features methods for identifying compounds that alter the activity of a nematode ATP synthase subunit E-like polypeptide. The method includes contacting the test compound to the nematode ATP synthase subunit E-like polypeptide; and detecting an ATP synthase subunit E-like activity. A decrease in the level of ATP synthase subunit E-like activity of the polypeptide relative to the level of ATP synthase subunit E-like activity of the polypeptide in the absence of the test compound is an indication that the test compound is an inhibitor of the ATP synthase subunit E-like activity. In still another embodiment, the method further includes contacting a test compound such as an allosteric inhibitor or other types of inhibitors that prevent binding of the ATP synthase subunit E-like polypeptide to other molecules or proteins. A change in activity of proteins normally bound by the subunit E is an indication that the test compound is an inhibitor of the ATP synthase subunit E-like activity. Such inhibitory compounds are potential selective agents for reducing the viability of a nematode expressing an ATP synthase subunit E-like polypeptide, e.g., the viability of *M. javanica, H. glycines,* and/or *Z. punctata*. These methods can also include contacting the compound with a mammalian (e.g., a human) ATP synthase subunit E-like polypeptide; and detecting an ATP synthase subunit E-like activity. A compound that decreases nematode ATP synthase subunit E activity to a greater extent than it decreases mammalian ATP synthase subunit E-like polypeptide activity could be useful as a selective inhibitor of the nematode polypeptide. A desirable compound can exhibit 2-fold, 5-fold, 10-fold, 20-fold, 50-fold, 100-fold or greater selective activity against the nematode polypeptide.

Another featured method is a method of screening for a compound that alters an activity of an ATP synthase subunit E-like polypeptide or alters binding or regulation of other polypeptides by ATP synthase subunit E. The method includes providing the polypeptide; contacting a test compound to the polypeptide; and detecting an ATP synthase subunit E-like activity or the activity of polypeptides bound or regulated by the subunit E (e.g., ATP synthase complex), wherein a change in activity of ATP synthase subunit E-like polypeptides or other downstream polypeptides relative to the ATP synthase subunit E-like activity of the polypeptide or downstream polypeptides (e.g., ATP synthase complex) in the absence of the test compound is an indication that the test compound alters the activity of the polypeptide(s). The method can further include contacting the test compound to a mammalian (e.g., a human) ATP synthase subunit E-like polypeptide and measuring the ATP synthase subunit E-like activity of the mammalian ATP synthase subunit E-like polypeptide or other polypeptides affected or regulated by the subunit E. A test compound that alters the activity of the nematode ATP synthase subunit E-like polypeptide at a given concentration and that does not substantially alter the activity of the mammalian ATP synthase subunit E-like polypeptide or downstream polypeptides at the given concentration can be identified. An additional method includes screening for both binding to an ATP synthase subunit E-like polypeptide and for an alteration in the activity of an ATP synthase subunit E-like polypeptide.

Yet another featured method is a method of screening for a compound that alters the viability or fitness of a transgenic cell or organism or nematode. The transgenic cell or organism has a transgene that expresses an ATP synthase subunit E-like polypeptide. The method includes contacting a test compound (e.g., an unscreened compound or one known to decrease ATP synthase subunit E activity in vitro) to the transgenic cell or organism and detecting changes in the viability or fitness of the transgenic cell or organism. This alteration in viability or fitness can be measured relative to an otherwise identical cell or organism that does not harbor the transgene.

Also featured is a method of screening for a compound that alters the expression of a nematode nucleic acid encoding an ATP synthase subunit E-like polypeptide, e.g., a nucleic acid encoding a *M. javanica, H. glycines*, and/or *Z. punctata* ATP synthase subunit E-like polypeptide. The method includes contacting a cell, e.g., a nematode cell, with a test compound and detecting expression of a nematode nucleic acid encoding an ATP synthase subunit E-like polypeptide, e.g., by hybridization to a probe complementary to the nematode nucleic acid encoding an ATP synthase subunit E-like polypeptide or by contacting polypeptides isolated from the cell with a compound, e.g., antibody that binds an ATP synthase subunit E-like polypeptide. Compounds identified by the method are also within the scope of the invention.

The screening methods described herein can further include exposing a nematode to the compound and assessing the effect of the compound on the viability or reproductive ability of the nematode. Such methods can entail exposing nematodes to those compounds which bind to, inhibit, reduce the espression of or otherwise interfere with ATP synthase subunit E-like activity. Compounds which reduce nematode viability or reproductive ability in such assays are candidate pesticides.

In yet another aspect, the invention features a method of treating a disorder (e.g., an infection) caused by a nematode, e.g., *M. javanica* or *H. glycines*, in a subject, e.g., a host plant or host animal. The method includes administering to the subject an effective amount of an inhibitor of an ATP synthase subunit E-like polypeptide activity or an inhibitor of expression of an ATP synthase subunit E-like polypeptide. Non-limiting examples of such inhibitors include: an antisense nucleic acid (or PNA) to an ATP synthase subunit E-like nucleic acid, an antibody to an ATP synthase subunit E-like polypeptide, or a small molecule identified as an ATP synthase subunit E-like polypeptide inhibitor by a method described herein.

A "purified polypeptide", as used herein, refers to a polypeptide that has been separated from other proteins, lipids, and nucleic acids with which it is naturally associated. The polypeptide can constitute at least 10, 20, 50 70, 80 or 95% by dry weight of the purified preparation.

An "isolated nucleic acid" is a nucleic acid, the structure of which is not identical to that of any naturally occurring nucleic acid, or to that of any fragment of a naturally occurring genomic nucleic acid spanning more than three, preferably one, separate genes. The term therefore covers, for example: (a) a DNA which is part of a naturally occurring genomic DNA molecule but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones in a DNA library such as a cDNA or genomic DNA library. Isolated nucleic acid molecules according to the present invention further include molecules produced synthetically, as well as any nucleic acids that have been altered chemically and/or that have modified backbones.

Although the phrase "nucleic acid molecule" primarily refers to the physical nucleic acid molecule and the phrase "nucleic acid sequence" refers to the sequence of the nucleotides in the nucleic acid molecule, the two phrases can be used interchangeably.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

The "percent identity" of two amino acid sequences or of two nucleic acids is determined using the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the BLASTN and BLASTX programs (version 2.0) of Altschul et al. (1990) *J. Mol. Biol.* 215:403-10. BLAST nucleotide searches can be performed with the BLASTN program, score=100, wordlength=12 to obtain nucleotide sequences homologous to the nucleic acid molecules of the invention. BLAST protein searches can be performed with the BLASTX program, score=50, wordlength=3 to obtain amino acid sequences homologous to the protein molecules of the invention. Where gaps exist between two sequences, Gapped BLAST can be utilized as described in Altschul et al. (1997) *Nucleic Acids Res.* 25:3389-3402. When utilizing BLAST and Gapped BLAST programs, the default parameters of the respective programs (e.g., BLASTX and BLASTN) can be used. Available on the internet at ncbi.nlm.nih.gov.

As used herein, the term "transgene" means a nucleic acid sequence (encoding, e.g., one or more subject polypeptides), which is partly or entirely heterologous, i.e., foreign, to the transgenic plant, animal, or cell into which it is introduced, or, is homologous to an endogenous gene of the transgenic plant, animal, or cell into which it is introduced, but which is designed to be inserted, or is inserted, into the plant's genome in such a way as to alter the genome of the cell into which it is inserted (e.g., it is inserted at a location which differs from that of the natural gene or its insertion results in a knockout). A transgene can include one or more transcriptional regulatory sequences and other nucleic acid sequences, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic plant" is any plant in which one or more, or all, of the cells of the plant includes a transgene. The transgene can be introduced into the cell, directly or indirectly by introduction into a precursor of the cell, by way of deliberate genetic manipulation, such as by T-DNA mediated transfer, electroporation, or protoplast transformation. The transgene may be integrated within a chromosome, or it may be extrachromosomally replicating DNA.

As used herein, the term "tissue-specific promoter" means a DNA sequence that serves as a promoter, i.e., regulates expression of a selected DNA sequence operably linked to the promoter, and which affects expression of the selected DNA sequence in specific cells of a tissue, such as a leaf, root, or stem.

As used herein, the terms "hybridizes under stringent conditions" and "hybridizes under high stringency conditions" refer to conditions for hybridization in 6× sodium chloride/sodium citrate (SSC) buffer at about 45° C., followed by two washes in 0.2×SSC buffer, 0.1% SDS at 60° C. or 65° C. As used herein, the term "hybridizes under low stringency conditions" refers to conditions for hybridization in 6×SSC buffer at about 45° C., followed by two washes in 6×SSC buffer, 0.1% (w/v) SDS at 50° C.

A "heterologous promoter", when operably linked to a nucleic acid sequence, refers to a promoter which is not naturally associated with the nucleic acid sequence.

As used herein, an agent with "anthelminthic activity" is an agent, which when tested, has measurable nematode-killing activity or results in infertility or sterility in the nematodes such that unviable or no offspring result. In the assay, the agent is combined with nematodes, e.g., in a well of microtiter dish having agar media or in the soil containing the agent. Staged adult nematodes are placed on the media. The time of survival, viability of offspring, and/or the movement of the nematodes are measured. An agent with "anthelminthic activity" reduces the survival time of adult nematodes relative to unexposed similarly staged adults, e.g., by about 20%, 40%, 60%, 80%, or more. In the alternative, an agent with "anthelminthic activity" may also cause the nematodes to cease replicating, regenerating, and/or producing viable progeny, e.g., by about 20%, 40%, 60%, 80%, or more.

As used herein, the term "binding" refers to the ability of a first compound and a second compound that are not covalently linked to physically interact. The apparent dissociation constant for a binding event can be 1 mM or less, for example, 10 nM, 1 nM, 0.1 nM or less.

As used herein, the term "binds specifically" refers to the ability of an antibody to discriminate between a target ligand and a non-target ligand such that the antibody binds to the target ligand and not to the non-target ligand when simultaneously exposed to both the given ligand and non-target ligand, and when the target ligand and the non-target ligand are both present in molar excess over the antibody.

As used herein, the term "altering an activity" refers to a change in level, either an increase or a decrease in the activity, (e.g., an increase or decrease in the ability of the polypeptide to bind or regulate other polypeptides or molecules) particularly an ATP synthase subunit E-like or ATP synthase subunit E activity. The change can be detected in a qualitative or quantitative observation. If a quantitative observation is made, and if a comprehensive analysis is performed over a plurality of observations, one skilled in the art can apply routine statistical analysis to identify modulations where a level is changed and where the statistical parameter, the p value, is less than 0.05.

In part, the nematode ATP synthase subunit E proteins and nucleic acids described herein are novel targets for anti-nematode vaccines, pesticides, and drugs. Inhibition of these molecules can provide means of inhibiting nematode metabolism and/or the nematode life-cycle.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 depicts the cDNA sequence of *M. javanica* ATP synthase subunit E (SEQ ID NO: 1), its corresponding encoded amino acid sequence (SEQ ID NO: 4), and its open reading frame (SEQ ID NO: 7).

FIG. 2 depicts the cDNA sequence of *H. glycines* ATP synthase subunit E (SEQ ID NO: 2), its corresponding encoded amino acid sequence (SEQ ID NO: 5), and its open reading frame (SEQ ID NO: 8).

FIG. 3 depicts the cDNA sequence of *Z. punctata* ATP synthase subunit E (SEQ ID NO: 3), its corresponding encoded amino acid sequence (SEQ ID NO: 6), and its open reading frame (SEQ ID NO: 9).

DETAILED DESCRIPTION

Figure 4:
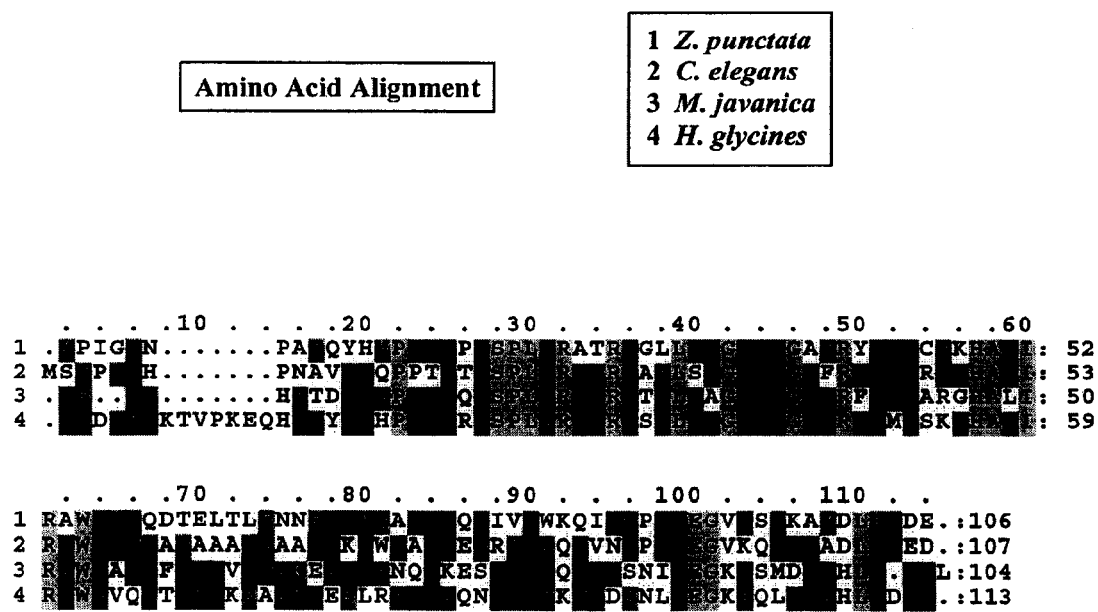
FIG. 4 is an alignment of the sequences of *M. javanica, H. glycines*, and *Z. punctata* ATP synthase subunit E-like polypeptides (SEQ ID NO: 4, 5, and 6) and *C. elegans* ATP synthase subunit E-like polypeptide (SEQ ID NO: 10).

ATP synthases of eubacteria, chloroplasts, and mitochondria synthesize ATP from ADP and inorganic phosphate using a transmembrane proton gradient to drive the reaction. In bacterial enzymes and in reconstituted mitochondrial enzymes the process is reversible and the enzymes can also hydrolyze ATP and use the energy released in the process to pump protons. The enzymes from various sources differ in complexity of their subunits. To date, the simplest ATP synthase to be described (FIFO synthase) is from *E. coli*. The FIFO synthase has eight different subunits. Five of the subunits form a globular catalytic subcomplex ($F_1$), and three others comprise the membrane bound domain of the enzyme ($F_0$) to which the catalytic $F_1$ subcomplex is bound. Proton flux through the $F_0$ subcomplex has been postulated to cause conformational changes, which may pass to the catalytic $F_1$ subcomplex through the stalk of the $F_0$ complex. While the overall architecture of the ATP synthases in higher invertebrates and vertebrates appears to be similar to that of bacterial ATP synthases, they are generally more complex and have a number of additional subunits. Mammalian mitochondrial ATP synthases, for example, include between 12 and 18 protein components (Walter et al. (1991) *Biochemistry* 30: 5369-5378).

One subunit suspected of having a regulatory role in a mammalian ATP synthases, perhaps in response to $Ca^{2+}$, is subunit E. Subunit E is a highly charged, basic protein that has been shown to be peripherally associated with the $F_0$ subcomplex of the mammalian $F_1F_0$-ATP synthase. Subunit E is thought to bind to the $F_O$ subcomplex and transmit conformational changes to the $F_1$ catalytic subcomplex. The regulatory role of subunit E is predicted based upon its differential regulation at the transcriptional level in response to such diverse conditions as hypoxia, UV irradiation, and high/low fat diets. Ultimately, regulation of the $F_OF_1$-ATP synthase, through subunit E and other subunits, leads to control of energy production, as would be expected of an enzyme involved in ATP synthesis (Elliot et al. (1993) Biochem Biophys. Res. Com. 190:167-174; Levy (1997) Amer. Phys. Soc. 457-465).

This invention describes a novel class of nematode genes related C. elegans protein T23910 (GenBank® Accession No: 7506279). The nematode genes can be shown by a PSI-BLAST bioinformatics analysis to be highly divergent members of the ATP synthase subunit E gene family. This divergent gene family appears to be restricted to higher metazoans (e.g., nematodes, arthropods, vertebrates) and is not detected in available sequences of fungi, bacteria or plants. We have identified additional homologs in the nematodes M. javanica, H. glycines and Z. punctata. Importantly, we have shown that these proteins are essential for the viability of C. elegans using RNAi interference, suggesting that these proteins are promising targets for anti-parasitic compounds.

As in the case of the mammalian proteins, the nematode homologs are small, hydrophilic proteins. Despite the low pairwise sequence identity over the entire length of molecule (below 30%) for several nematode-vertebrate comparisons, a multiple alignment of all ATP synthase subunit E-like proteins shows regions of similarity, as well as absolute conservation in some regions (particularly in the amino terminus). Another quality shared among the members of this family is the lack of a mitochondrial pro-sequence. Instead, the proteins are all predicted to contain putative transmembrane regions in their N-terminal regions (by TMHMM, available on the Internet at cbs.dtu.dk/services/TMHMM/), which can be recognized as a weak preference for mitochondrial localization in some cases (by Target P, available on the Internet at cbs.dtu.dk/services/TargetP/).

The present invention provides nucleic acids from nematodes encoding ATP synthase subunit E-like polypeptides. The M. javanica nucleic acid molecule (SEQ ID NO: 1) and the encoded ATP synthase subunit E-like polypeptide (SEQ ID NO: 4) are depicted in FIG. 1. The H. glycines nucleic acid molecule (SEQ ID NO: 2) and the ATP synthase subunit E-like polypeptide (SEQ ID NO: 5) are depicted in FIG. 2. The Z. punctata nucleic acid molecule (SEQ ID NO: 3) and the ATP synthase subunit E-like polypeptide (SEQ ID NO: 6) are depicted in FIG. 3. Certain sequence information for the ATP synthase subunit E genes described herein is summarized in Table 1, below.

TABLE 1

ATP Synthase Subunit E Sequences

| Species | cDNA | ORF | Polypeptide | Figure |
|---|---|---|---|---|
| M. javanica | SEQ ID NO: 1 | SEQ ID NO: 7 | SEQ ID NO: 4 | FIG. 1 |
| H. glycines | SEQ ID NO: 2 | SEQ ID NO: 8 | SEQ ID NO: 5 | FIG. 2 |
| Z. punctata | SEQ ID NO: 3 | SEQ ID NO: 9 | SEQ ID NO: 6 | FIG. 3 |

The invention is based, in part, on the discovery of ATP synthase subunit E-like sequences from M. javanica, H. glycines, and Z. punctata. The following examples are, therefore, to be construed as merely illustrative, and not limitative of the remainder of the disclosure in any way whatsoever. All of the publications cited herein are hereby incorporated by reference in their entirety.

EXAMPLES

A TBLASTN query with the C. elegans gene T23910 (GenBank® GI: 7506279) identified multiple expressed sequence tags (ESTs are short nucleic acid fragment sequences from single sequencing reads) in dbest that are predicted to encode a portion of ATP synthase subunit E-like enzymes in at least three nematode species: M. javanica (GenBank® GI:9829776) similar to C. elegans codons 12-104; H. glycines (GenBank® GI:10713753) similar to C. elegans codons 6-104; and Z. punctata (GenBanks GI:7710479) similar to C. elegans codons 15-107, all from McCarter, et al. (1999) Washington University Nematode EST Project. Also identified were sequences from Pristionchus pacificus (GenBank® Identification No:5914683) similar to C. elegans codons 6-107; Strongyloides stercoralis (GenBank® GI:10715244) similar to C. elegans codons 1-107; Ancylostoma caninum (GenBank® GI:11180617) similar to C. elegans codons 49-107 (all from McCarter et al. (1999) Washington University Nematode EST Project), Litomosoides sigmodontis (GenBank® GI:6200636) similar to C. elegans codons 1-58 (from Allen et al. (2000) Infect. Immun. 68:5454-8); and Brugia malayi (GenBank® GI:1592572) similar to C. elegans codons 8-58 were also identified in dbest.

Full Length ATP Synthase Subunit E-Like cDNA Sequences

Plasmid clone Div348, corresponding to the M. javanica EST sequence (GI: 9829776) was obtained from the Genome Sequencing Center (St. Louis, Mo.). Similarly, plasmid clone Div361, corresponding to the H. glycines EST sequence (GI: 10713753), and plasmid clone Div222, corresponding to the Z. punctata EST sequence (GI: 7710479), were also obtained from the Genome Sequencing Center (St. Louis, Mo.). The cDNA inserts in the plasmids were sequenced in their entirety to obtain full-length sequences for ATP synthase subunit E-like genes from M. javanica (SEQ ID NO: 1), H. glycines (SEQ ID NO:2), and Z. punctata (SEQ ID NO:3).

Unless otherwise indicated, all nucleotide sequences determined herein were sequenced with an automated DNA sequencer (such as model 373 from Applied Biosystems, Inc.) using processes well-known to those skilled in the art. Primers used for sequencing are listed in Table 2, below.

TABLE 2

Sequencing Primers

| Name | Sequence | SEQ ID NO: | Homology to |
|---|---|---|---|
| T7 | gtaatacgactcactatagggc | 11 | vector polylinker primer |
| T3 | aattaaccctcactaaaggg | 12 | vector polylinker primer |
| SL1 | gggtttaattacccaagtttga | 13 | nematode transpliced leader |
| Oligo dT | gagagagagagagagagagaactagtctcgagttttttttttttttttttt | 14 | universal primer to poly A tail |

Characterization of M. javanica, H. glycyines, and Z. punctata ATP Synthase Subunit E The sequences of three ATP synthase subunit E-like nucleic acid molecules are depicted in FIG. 1, FIG. 2, and FIG. 3 as SEQ ID NO: 1, SEQ ID NO: 2, and SEQ ID NO: 3, respectively. SEQ ID NO: 7 contains an open reading frame encoding a 104 amino acid polypeptide, SEQ ID NO: 8 contains open reading frame encoding a 113 amino acid polypeptide, and SEQ ID NO: 9 contains an open reading frame encoding a 106 amino acid polypeptide.

The sequence of the *M. javanica* ATP synthase subunit E-like cDNA (SEQ ID NO: 1) is depicted in FIG. 1. This nucleotide sequence also contains an open reading frame (SEQ ID NO:7) encoding a 104 amino acid polypeptide (SEQ ID NO:4). The *M. javanica* ATP synthase subunit E-like protein sequence (SEQ ID NO: 4) is also approximately 38% identical to the *C. elegans* ATP synthase subunit E-like gene (SEQ ID NO: 10).

The sequence of the *H. glycines* ATP synthase subunit E-like cDNA (SEQ ID NO:2) is depicted in FIG. 2. This nucleotide sequence contains an open reading frame (SEQ ID NO:8) encoding a 113 amino acid polypeptide (SEQ ID NO:5). The *H. glycines* ATP synthase subunit E-like protein sequence (SEQ ID NO: 5) is approximately 41% identical to the *C. elegans* ATP synthase subunit E-like gene (SEQ ID NO: 10).

The sequence of the *Z. punctata* ATP synthase subunit E-like cDNA (SEQ ID NO:3) is depicted in FIG. 3. This nucleotide sequence contains an open reading frame (SEQ ID NO:9) encoding a 106 amino acid polypeptide (SEQ ID NO:6). The *Z. punctata* ATP synthase subunit E-like protein sequence (SEQ ID NO: 6) is approximately 36% identical to the *C. elegans* ATP synthase subunit E-like gene (SEQ ID NO: 10).

The similarity among the *M. javanica, H. glycines, Z. punctata*, and *C. elegans* polypeptides is presented as a multiple alignment generated by Clustal X multiple alignment program as described below (FIG. 4).

The similarity between *M. javanica, H. glycines*, and *Z. punctata* ATP synthase subunit E-like sequences and other sequences was also investigated by comparison to sequence databases using BLASTP analysis against nr (a non-redundant protein sequence database available on the Internet at ncbi.nlm.nih.gov/) and TBLASTN analysis against dbest (an EST sequence database available on the Internet at ncbi.nlm.nih.gov/; top 500 hits; E=1 e-4). The "Expect (E) value" is the number of sequences that are predicted to align by chance to the query sequence with a score S or greater given the size of the database queried. This analysis was used to determine the potential number of plant and vertebrate homologs for each of the nematode ATP synthase subunit E-like polypeptides described above. *M. javanica* (SEQ ID NO: 1), *H. glycines* (SEQ ID NO: 2), *Z. punctata* (SEQ ID NO: 3), and *C. elegans* (SEQ ID NO: 10) ATP synthase subunit E-like sequences had no vertebrate and/or plant hits in nr or dbest having sufficient sequence similarity to meet the threshold E value of 1 e–4 (this E value approximately corresponds to a threshold for removing sequences having a sequence identity of less than about 25% over approximately 100 amino acids). Accordingly, the *M. javanica, H. glycines*, and/or *Z. punctata* ATP synthase subunit E-like enzymes of this invention do not appear to share significant sequence similarity with the more common vertebrate forms of the enzyme such as the *Homo sapiens* (GenBank® GI:6005717; GenBank® Accession No: NP_009031.1) or the *Rattus norvegicus* (GenBank® Accession No: P29419) ATP synthase subunit E.

On the basis of the lack of similarity to plants and vertebrates, the *M. javanica, H. glycines*, and/or *Z. punctata* ATP synthase subunit E-like enzymes are useful targets of inhibitory compounds selective for some nematodes over their hosts (e.g., humans, animals, and plants).

Functional predictions were made using four iterations of PSI-BLAST with the default parameters on the nr database. PSI-BLAST searches and multiple alignment construction with CLUSTALX demonstrated that the *C. elegans* gene (GenBank® Accession No: T23910) was a member of the ATP synthase subunit E family. Reciprocal blast searches and phylogenetic trees confirm that the nucleotide sequences in *M. javanica, H. glycines*, and/or *Z. punctata* do encode orthologs of the *C. elegans* gene and therefore also likely ATP synthase subunit E proteins. Protein localizations were predicted using the TargetP server available on the Internet at cbs.dtu.dk/services/TargetP/). The *M. javanica, H. glycines*, and/or *Z. punctata* ATP synthase subunit E (SEQ ID NO: 4, 5, and 6, respectively) polypeptides are potentially mitochondrial based on the presence of putative transmembrane domain in the amino-terminus and the fact that all other proteins in the family have weak mitochondrial signals and putative transmembrane domains in the N-terminus.

RNA Mediated Interference (RNAi) A double stranded RNA (dsRNA) molecule can be used to inactivate a subunit E-like gene in a cell by a process known as RNA mediated-interference (Fire et al. (1998) *Nature* 391:806-811, and Gönczy et al. (2000) *Nature* 408:331-336). The dsRNA molecule can have the nucleotide sequence of a subunit E-like nucleic acid described herein or a fragment thereof. For example, the molecule can comprise at least 50, at least 100, at least 200, at least 300, or at least 500 or more contiguous nucleotides of a subunit E-like gene. The dsRNA molecule can be delivered to nematodes via direct injection, by soaking nematodes in aqueous solution containing concentrated dsRNA, or by raising bacteriovorous nematodes on *E. coli* genetically engineered to produce the dsRNA molecule (Kamath et al. (2000) *Genome Biol.* 2; Tabara et al. (1998) *Science* 282:430-431).

*C. elegans* were grown on lawns of *E. coli* genetically engineered to produce double stranded RNA designed to inhibit ATP synthase subunit expression. *E. coli* were transformed with a 437 nucleotide genomic fragment of the subunit E-like gene. The genomic fragment included 255 nucleotides of exon sequence and 182 nucleotides of intron sequence (58% exon overall). The exonic sequences correspond to the first 115 nucleotides of SEQ ID NO:4, followed by 182 nucleotides of intronic sequence (interrupting the glycine codon at position 39) and then by 140 nucleotides of additional exonic sequence (ending at the glutamine codon at position 85). The 437 nucleotide genomic fragment was cloned into an *E. coli* expression vector between opposing T7 polymerase promoters, and the vector was transformed into a strain of *E. coli* that carries an IPTG-inducible T7 polymerase. As a control, *E. coli* was transformed with a gene encoding the Green Fluorescent Protein (GFP). GFP is a commonly used reporter gene originally isolated from jellyfish and is widely used in both prokaryotic and eukaryotic systems. The GFP gene is not present in the wild-type *C. elegans* genome and thus it does not trigger an RNAi phenotype when ingested by *C. elegans*. In both samples, *C. elegans* was grown at 15° C. on NGM plates containing IPTG and *E. coli* expressing the subunit E-like specific dsRNA or GFP. Total eggs layed and hatch-rates of F1 and F2 individuals were followed over the course of 7-10 days (as shown below) and compared to nematode cultures grown on non-toxic dsRNAs.

In another example, dsRNA was injected into the nematode, basically as described in Mello et al. (1991) *EMBO J.* 10:3959-3970. In short, a plasmid was constructed that contains a portion of the *C. elegans* gene sequence, specifically a fragment 437 nucleotides long, containing 115 nucleotides of the first exon followed by the first intron of 182 nucleotides and 140 nucleotides of the second exon (58% exon sequence) corresponding to amino acid positions 1-85. The TOPO vector and PCR primers corresponding to the T7 and SP6 regions were to specifically amplify this sequence as a linear dsDNA. Single-strand RNAs can be transcribed from this fragment using either T7 RNA polymerase or SP6 RNA polymerase (the RNAs correspond to the sense and antisense RNA strands). RNA so produced was precipitated and resuspended in RNAse free water. SsRNAs were combined, heated to 95° C. for two minutes then allowed to cool from 70° C. to room temperature over 1.5-2.5 hours.

DsRNA was injected into the body cavity of 15-20 young adult *C. elegans* hermaphrodites. Worms were typically immobilized on an agarose pad and injected with 2-5 nanoliters of dsRNA at a concentration of 1 mg/ml. Injections were performed with visual observation using a Zeiss Axiovert compound microscope equipped with 10× and 40×DIC objectives. Needles for microinjection were prepared using a Narishige needle puller, stage micromanipulator (Leitz) and an N2-powered injector (Narishige) set at 10-20 p.s.i. After injection, 200 µl of recovery buffer (0.1% salmon sperm DNA, 4% glucose, 2.4 mM KCl, 66 mM NaCl, 3 mM CaCl$_2$, 3 mM HEPES, pH 7.2) was added to the agarose pad and the worms were allowed to recover on the agarose pad for 0.5-4 hours. After recovery, the worms were transferred to NGM agar plates seeded with a lawn of *E. coli* strain OP50 as a food source. The following day and for 3 successive days thereafter, 7 individual healthy injected worms were transferred to new NGM plates seeded with OP50. The number of eggs laid per worm per day and the number of those eggs that hatch and reach fertile adulthood can be determined. As a control, GFP dsRNA was produced and injected using similar methods.

The results of the studies described above were as follows.

Feeding RNAi:

Experiment F8-D403 (ATP synthetase subunit E-like RNA)
Total # worms monitored: 6
Total # eggs layed: 171
Total # eggs hatched: 2
Hatch %:1.2%

Experiment F8-D334 (GFP control RNA)
Total # worms monitored: 6
Total # eggs layed: 527
Total # eggs hatched: 526
Hatch %:99.8%
Injection RNAi:

Experiment J332 (ATP synthetase subunit-like RNA)
Total # worms monitored: 7
Total # eggs layed: 141
Total # eggs hatched: 0
Hatch %: 0.0%

Experiment J335 (GFP control RNA)
Total # worms monitored: 8
Total # eggs layed: 798
Total # eggs hatched: 789
Hatch %: 98.9%

As the results demonstrate, *C. elegans* cultures grown in the presence of *E. coli* expressing dsRNA and those injected with dsRNA from the subunit E-like gene were strongly impaired indicating that the subunit E-like gene provides an essential function in nematodes and that dsRNA from the subunit E-like gene is lethal when ingested by or injected into *C. elegans*.

These results demonstrate that ATP synthase subunit E is important for the viability of *C. elegans* and suggest that it is a useful target for the development of compounds that reduce the viability of nematodes.

Identification of Additional ATP Synthase Subunit E-Like Sequences

A skilled artisan can utilize the methods provided in the example above to identify additional nematode ATP synthase subunit E-like sequences, e.g., ATP synthase subunit E-like sequence from nematodes other than *M. javanica, H. glycines, Z. punctata* and/or *C. elegans*. In addition, nematode ATP synthase subunit E-like sequences can be identified by a variety of methods including computer-based database searches, hybridization-based methods, and functional complementation.

Database Identification. A nematode ATP synthase subunit E-like sequence can be identified from a sequence database, e.g., a protein or nucleic acid database using a sequence disclosed herein as a query. Sequence comparison programs can be used to compare and analyze the nucleotide or amino acid sequences. One such software package is the BLAST suite of programs from the National Center for Biotechnology Institute (NCBI; Altschul et al. (1997) *Nucl. Acids Research* 25:3389-3402). An ATP synthase subunit E-like sequence of the invention can be used to query a sequence database, such as nr, dbest (expressed sequence tag (EST) sequences), and htgs (high-throughput genome sequences), using a computer-based search, e.g., FASTA, BLAST, or PSI-BLAST search. Homologous sequences in other species (e.g., humans and animals) can be detected in a PSI-BLAST search of a database such as nr (E value=10, H value=1e-2, using, for example, four iterations; available at the NIH webpage). Sequences so obtained can be used to construct a multiple alignment, e.g., a ClustalX alignment, and/or to build a phylogenetic tree, e.g., in ClustalX using the Neighbor-Joining method (Saitou et al. (1987) *Mol. Biol. Evol.* 4:406-425) and bootstrapping (1000 replicates; Felsenstein (1985) *Evolution* 39:783-791). Distances may be corrected for the occurrence of multiple substitutions [$D_{corr}$=-ln(1D-D$^2$/5) where D is the fraction of amino acid differences between two sequences] (Kimura (1983) *The Neutral Theory of Molecular Evolution*, Cambridge University Press).

The aforementioned search strategy can be used to identify ATP synthase subunit E-like sequences in nematodes of the following non-limiting, exemplary genera: Plant nematode genera: *Afrina, Anguina, Aphelenchoides, Belonolaimus, Bursaphelenchus, Cacopaurus, Cactodera, Criconema, Criconemoides, Cryphodera, Ditylenchus, Dolichodorus, Dorylaimus, Globodera, Helicotylenchus, Hemicriconemoides, Hemicycliophora, Heterodera, Hirschmanniella, Hoplolaimus, Hypsoperine, Longidorus, Meloidogyne, Mesoanguina, Nacobbus, Nacobbodera, Panagrellus, Paratrichodorus, Paratylenchus, Pratylenchus, Pterotylenchus, Punctodera, Radopholus, Rhadinaphelenchus, Rotylenchulus, Rotylenchus, Scutellonema, Subanguina, Thecavermiculatus, Trichodorus, Turbatrix, Tylenchorhynchus, Tylenchulus, Xiphinema.*

Animal and human nematode genera: *Acanthocheilonema, Aelurostrongylus, Ancylostoma, Angiostrongylus, Anisakis, Ascaris, Ascarops, Bunostomum, Brugia, Capillaria, Chabertia, Cooperia, Crenosoma, Cyathostome* species (Small Strongyles), *Dictyocaulus, Dioctophyma, Dipetalonema, Dirofilaria, Dracunculus, Draschia, Elaneophora, Enterobius, Filaroides, Gnathostoma, Gonylonema, Habronema, Haemonchus, Hyostrongylus, Lagochilascaris, Litomosoides, Loa, Mammomonogamus, Mansonella, Muelle-* rius, Metastrongylid, Necator, Nematodirus, Nippostrongylus, Oesophagostomum, Ollulanus, Onchocerca, Ostertagia, Oxyspirura, Oxyuris, Parafilaria, Parascaris, Parastrongyloides, Parelaphostrongylus, Physaloptera, Physocephalus, Protostrongylus, Pseudoterranova, Setaria, Spirocerca, Stephanurus, Stephanofilaria, Strongyloides, Strongylus, Spirocerca, Syngamus, Teladorsagia, Thelazia, Toxascaris, Toxocara, Trichinella, Trichostrongylus, Trichuris, Uncinaria,* and *Wuchereria*.

Particularly preferred nematode genera include: Plant: *Anguina, Aphelenchoides, Belonolaimus, Bursaphelenchus, Ditylenchus, Dolichodorus, Globodera, Heterodera, Hoplolaimus, Longidorus, Meloidogyne, Nacobbus, Pratylenchus, Radopholus, Rotylenchus, Tylenchulus, Xiphinema.*

Animal and human: *Ancylostoma, Ascaris, Brugia, Capillaria, Cooperia, Cyathostome* species, *Dictyocaulus, Dirofiliaria, Dracunculus, Enterobius, Haemonchus, Necator, Nematodirus, Oesophagostomum, Onchocerca, Ostertagia, Oxyspirura, Oxyuris, Parascaris, Strongyloides, Strongylus, Syngamus, Teladorsagia, Thelazia, Toxocara, Trichinella, Trichostrongylus, Trichuris,* and *Wuchereria*.

Particularly preferred nematode species include: Plant: *Anguina tritici, Aphelenchoides fragariae, Belonolaimus longicaudatus, Bursaphelenchus xylophilus, Ditylenchus destructor, Ditylenchus dipsaci Dolichodorus heterocephalous, Globodera pallida, Globodera rostochiensis, Globodera tabacum, Heterodera avenae, Heterodera cardiolata, Heterodera carotae, Heterodera cruciferae, Heterodera glycines, Heterodera major, Heterodera schachtii, Heterodera zeae, Hoplolaimus tylenchiformis, Longidorus sylphus, Meloidogyne acronea, Meloidogyne arenaria, Meloidogyne chitwoodi, Meloidogyne exigua, Meloidogyne graminicola, Meloidogyne hapla, Meloidogyne incognita, Meloidogyne javanica, Meloidogyne nassi, Nacobbus batatiformis, Pratylenchus brachyurus, Pratylenchus coffeae, Pratylenchus penetrans, Pratylenchus scribneri, Pratylenchus zeae, Radopholus similis, Rotylenchus reniformis, Tylenchulus semipenetrans, Xiphinema americanum.*

Animal and human: *Ancylostoma braziliense, Ancylostoma caninum, Ancylostoma ceylanicum, Ancylostoma duodenale, Ancylostoma tubaeforme, Ascaris suum, Ascaris lumbrichoides, Brugia malayi, Capillaria bovis, Capillaria plica, Capillaria feliscati, Cooperia oncophora, Cooperia punctata, Cyathostome* species, *Dictyocaulus filaria, Dictyocaulus viviparus, Dictyocaulus arnfieldi, Dirofiliaria immitis, Dracunculus insignis, Enterobius vermicularis, Haemonchus contortus, Haemonchus placei, Necator americanus, Nematodirus helvetianus, Oesophagostomum radiatum, Onchocerca volvulus, Onchocerca cervicalis, Ostertagia ostertagi, Ostertagia circumcincta, Oxyuris equi, Parascaris equorum, Strongyloides stercoralis, Strongylus vulgaris, Strongylus edentatus, Syngamus trachea, Teladorsagia circumcincta, Toxocara cati, Trichinella spiralis, Trichostrongylus axei, Trichostrongylus colubriformis, Trichuris vulpis, Trichuris suis, Trichurs trichiura,* and *Wuchereria bancrofti.*

Further, an ATP synthase subunit E-like sequence can be used to identify additional ATP synthase subunit E-like sequence homologs within a genome. Multiple homologous copies of an ATP synthase subunit E-like sequence can be present. For example, a nematode ATP synthase subunit E-like sequence can be used as a seed sequence in an iterative PSI-BLAST search (default parameters, substitution matrix=Blosum62, gap open=11, gap extend=1) of a non redundant database such as wormpep (E value=1e−2, H value=1e−4, using, for example 4 iterations) to determine the number of homologs in a database, e.g., in a database containing the complete genome of an organism. A nematode ATP synthase subunit E-like sequence can be present in a genome along with 1, 2, 3, 4, 5, 6, 8, 10, or more homologs.

Hybridization Methods. A nematode ATP synthase subunit E-like sequence can be identified by a hybridization-based method using a sequence provided herein as a probe. For example, a library of nematode genomic or cDNA clones can be hybridized under low stringency conditions with the probe nucleic acid. Stringency conditions can be modulated to reduce background signal and increase signal from potential positives. Clones so identified can be sequenced to verify that they encode ATP synthase subunit E-like sequences.

Another hybridization-based method utilizes an amplification reaction (e.g., the polymerase chain reaction (PCR)). Oligonucleotides, e.g., degenerate oligonucleotides, are designed to hybridize to a conserved region of an ATP synthase subunit E-like sequence (e.g., a region conserved in the three nematode sequences depicted in FIG. 4). The oligonucleotides are used as primers to amplify an ATP synthase subunit E-like sequence from template nucleic acid from a nematode, e.g., a nematode other than *M. javanica, H. glycines, Z. punctata,* and/or *C. elegans.* The amplified fragment can be cloned and/or sequenced.

Complementation Methods. A nematode ATP synthase subunit E-like sequence can be identified from a complementation screen for a nucleic acid molecule that restores ATP synthase subunit E-like activity to a cell lacking an ATP synthase subunit E-like activity. Routine methods can be used to construct strains (i.e., nematode strains) that lack specific enzymatic activities, e.g., ATP synthase subunit E activity. For example, a nematode strain mutated at the ATP synthase subunit E gene locus can be identified by selecting for resistance to inhibitory compounds and/or compounds that prevent the subunit E from binding to and thus, regulating, activity of an ATP synthase. Such a strain can be transformed with a plasmid library expressing nematode cDNAs. Strains can be identified in which ATP synthase subunit E activity is restored. For example, the ATP synthase subunit E mutant strains transformed with the plasmid library can be exposed to allosteric inhibitors or other inhibitory compounds to select for strains that have acquired sensitivity to the inhibitors and are expressing a nematode ATP synthase subunit E-like gene. The plasmid harbored by the strain can be recovered to identify and/or characterize the inserted nematode cDNA that provides ATP synthase subunit E-like activity when expressed.

Full-length cDNA and Sequencing Methods. The following methods can be used, e.g., alone or in combination with another method described herein, to obtain full-length nematode ATP synthase subunit E-like genes and determine their sequences.

Plant parasitic nematodes are maintained on greenhouse pot cultures depending on nematode preference. Root Knot Nematodes (*Meloidogyne* sp) are propagated on Rutgers tomato (Burpee), while Soybean Cyst Nematodes (*Heterodera* sp) are propagated on soybean. Total nematode RNA is isolated using the TRIZOL reagent (Gibco BRL). Briefly, 2 ml of packed worms are combined with 8 ml TRIZOL reagent and solubilized by vortexing. Following 5 minutes of incubation at room temperature, the samples are divided into smaller volumes and spun at 14,000×g for 10 minutes at 4° C. to remove insoluble material. The liquid phase is extracted with 200 µl of chloroform, and the upper aqueous phase is removed to a fresh tube. The RNA is precipitated by the addition of 500 µl of isopropanol and centrifuged to pellet. The aqueous phase is carefully removed, and the pellet is washed in 75% ethanol and spun to re-collect the RNA pellet. The supernatant is carefully removed, and the pellet is air dried for 10 minutes. The RNA pellet is resuspended in 50 μl of DEPC—H2O and analyzed by spectrophotometry at λ 260 and 280 nm to determine yield and purity. Yields can be 1-4 mg of total RNA from 2 ml of packed worms.

Full-length cDNAs can be generated using 5' and 3' RACE techniques in combination with EST sequence information. The molecular technique 5' RACE (Life Technologies, Inc., Rockville, Md.) can be employed to obtain complete or near-complete 5' ends of cDNA sequences for nematode ATP synthase subunit E-like cDNA sequences. Briefly, following the instructions provided by Life Technologies, first strand cDNA is synthesized from total nematode RNA using Murine Leukemia Virus Reverse Transcriptase (M-MLV RT) and a gene specific "antisense" primer, e.g., designed from available EST sequence. RNase H is used to degrade the original mRNA template. The first strand cDNA is separated from unincorporated dNTPs, primers, and proteins using a Glass-MAX Spin Cartridge. Terminal deoxynucleotidyl transferase (TdT) is used to generate a homopolymeric dC tailed extension by the sequential addition of dCTP nucleotides to the 3' end of the first strand cDNA. Following addition of the dC homopolymeric extension, the first strand cDNA is directly amplified without further purification using Taq DNA polymerase, a gene specific "antisense" primer designed from available EST sequences to anneal to a site located within the first strand cDNA molecule, and a deoxyinosine-containing primer that anneals to the homopolymeric dC tailed region of the cDNA in a polymerase chain reaction (PCR). 5' RACE PCR amplification products are cloned into a suitable vector for further analysis and sequencing.

The molecular technique, 3' RACE (Life Technologies, Inc., Rockville, Md.), can be employed to obtain complete or near-complete 3' ends of cDNA sequences for nematode ATP synthase subunit E-like cDNA sequences. Briefly, following the instructions provided by Life Technologies (Rockville, Md.), first strand cDNA synthesis is performed on total nematode RNA using SuperScript™ Reverse Transcriptase and an oligo-dT primer that anneals to the polyA tail. Following degradation of the original mRNA template with RNase H, the first strand cDNA is directly PCR amplified without further purification using Taq DNA polymerase, a gene specific primer designed from available EST sequences to anneal to a site located within the first strand cDNA molecule, and a "universal" primer which contains sequence identity to 5' end of the oligo-dT primer. 3' RACE PCR amplification products are cloned into a suitable vector for further analysis and sequencing.

Nucleic Acid Variants

Isolated nucleic acid molecules of the present invention include nucleic acid molecules that have an open reading frame encoding an ATP synthase subunit E-like polypeptide. Such nucleic acid molecules include molecules having: the sequences recited in SEQ ID NO: 1, 2, and/or 3; and sequences coding for the ATP synthase subunit E-like proteins recited in SEQ ID NO: 4, 5, and/or 6. These nucleic acid molecules can be used, for example, in a hybridization assay to detect the presence of a M. javanica, H. glycines, and/or Z. punctata nucleic acid in a sample.

The present invention includes nucleic acid molecules such as those shown in SEQ ID NO: 1, 2, and/or 3 that may be subjected to mutagenesis to produce single or multiple nucleotide substitutions, deletions, or insertions. Nucleotide insertional derivatives of the nematode gene of the present invention include 5' and 3' terminal fusions as well as intra-sequence insertions of single or multiple nucleotides. Insertional nucleotide sequence variants are those in which one or more nucleotides are introduced into a predetermined site in the nucleotide sequence, although random insertion is also possible with suitable screening of the resulting product. Deletion variants are characterized by the removal of one or more nucleotides from the sequence. Nucleotide substitution variants are those in which at least one nucleotide in the sequence has been removed and a different nucleotide inserted in its place. Such a substitution may be silent (e.g., synonymous), meaning that the substitution does not alter the amino acid defined by the codon. Alternatively, substitutions are designed to alter one amino acid for another amino acid (e.g., non-synonymous). A non-synonymous substitution can be conservative or non-conservative. A substitution can be such that activity, e.g., a ATP synthase subunit E-like activity, is not impaired. A conservative amino acid substitution results in the alteration of an amino acid for a similar acting amino acid, or amino acid of like charge, polarity, or hydrophobicity, e.g., an amino acid substitution listed in Table 3 below. At some positions, even conservative amino acid substitutions can disrupt the activity of the polypeptide.

TABLE 3

Conservative Amino Acid Replacements

| For Amino | Code | Replace with any of |
| --- | --- | --- |
| Alanine | Ala | Gly, Cys, Ser |
| Arginine | Arg | Lys, His |
| Asparagine | Asn | Asp, Glu, Gln, |
| Aspartic Acid | Asp | Asn, Glu, Gln |
| Cysteine | Cys | Met, Thr, Ser |
| Glutamine | Gln | Asn, Glu, Asp |
| Glutamic Acid | Glu | Asp, Asn, Gln |
| Glycine | Gly | Ala |
| Histidine | His | Lys, Arg |
| Isoleucine | Ile | Val, Leu, Met |
| Leucine | Leu | Val, Ile, Met |
| Lysine | Lys | Arg, His |
| Methionine | Met | Ile, Leu, Val |
| Phenylalanine | Phe | Tyr, His, Trp |
| Proline | Pro | |
| Serine | Ser | Thr, Cys, Ala |
| Threonine | Thr | Ser, Met, Val |
| Tryptophan | Trp | Phe, Tyr |
| Tyrosine | Tyr | Phe, His |
| Valine | Val | Leu, Ile, Met |

The current invention also embodies splice variants of nematode ATP synthase subunit E-like sequences.

Another aspect of the present invention embodies a polypeptide-encoding nucleic acid molecule that is capable of hybridizing under conditions of low stringency (or high stringency) to the nucleic acid molecule put forth in SEQ ID NO: 1, 2, and/or 3, or their complements.

The nucleic acid molecules that encode for ATP synthase subunit E-like polypeptides may correspond to the naturally occurring nucleic acid molecules or may differ by one or more nucleotide substitutions, deletions, and/or additions. Thus, the present invention extends to genes and any functional mutants, derivatives, parts, fragments, naturally occurring polymorphisms, homologs or analogs thereof or non-functional molecules. Such nucleic acid molecules can be used to detect polymorphisms of ATP synthase subunit E genes or ATP synthase subunit E-like genes, e.g., in other nematodes. As mentioned below, such molecules are useful as genetic probes; primer sequences in the enzymatic or chemical synthesis of the gene; or in the generation of immunologically interactive recombinant molecules. Using the information provided herein, such as the nucleotide sequence SEQ ID NO: 1, 2, and/or 3, a nucleic acid molecule encoding an ATP synthase subunit E-like molecule may be obtained using standard cloning and a screening techniques, such as a method described herein.

Nucleic acid molecules of the present invention can be in the form of RNA, such as mRNA, or in the form of DNA, including, for example, cDNA and genomic DNA obtained by cloning or produced synthetically. The DNA may be double-stranded or single-stranded. The nucleic acids may be in the form of RNA/DNA hybrids. Single-stranded DNA or RNA can be the coding strand, also referred to as the sense strand, or the non-coding strand, also known as the anti-sense strand.

One embodiment of the present invention includes a recombinant nucleic acid molecule, which includes at least one isolated nucleic acid molecule depicted in SEQ ID NO: 1, 2, and/or 3, inserted in a vector capable of delivering and maintaining the nucleic acid molecule into a cell. The DNA molecule may be inserted into an autonomously replicating vector (suitable vectors include, for example, pGEM3Z and pcDNA3, and derivatives thereof). The vector nucleic acid may be a bacteriophage DNA such as bacteriophage lambda or M13 and derivatives thereof. The vector may be either RNA or DNA, single- or double-stranded, prokaryotic, eukaryotic, or viral. Vectors can include transposons, viral vectors, episomes, (e.g., plasmids), chromosomes inserts, and artificial chromosomes (e.g. BACs or YACs). Construction of a vector containing a nucleic acid described herein can be followed by transformation of a host cell such as a bacterium. Suitable bacterial hosts include, but are not limited to, E. coli. Suitable eukaryotic hosts include yeast such as S. cerevisiae, other fungi, vertebrate cells, invertebrate cells (e.g., insect cells), plant cells, human cells, human tissue cells, and whole eukaryotic organisms. (e.g., a transgenic plant or a transgenic animal). Further, the vector nucleic acid can be used to generate a virus such as vaccinia or baculovirus.

The present invention also extends to genetic constructs designed for polypeptide expression. Generally, the genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art and may be functional in, but are not limited to, a bacterium, yeast, plant, or animal cell. The expression vector can also include a translation regulatory sequence (e.g., an untranslated 5' sequence, an untranslated 3' sequence, a poly A addition site, or an internal ribosome entry site), a splicing sequence or splicing regulatory sequence, and a transcription termination sequence. The vector can be capable of autonomous replication or it can integrate into host DNA.

In an alternative embodiment, the DNA molecule is fused to a reporter gene such as β-glucuronidase gene, β-galactosidase (lacZ), chloramphenicol-acetyltransferase gene, a gene encoding green fluorescent protein (and variants thereof), or red fluorescent protein firefly luciferase gene, among others. The DNA molecule can also be fused to a nucleic acid encoding a polypeptide affinity tag, e.g. glutathione S-transferase (GST), maltose E binding protein, protein A, FLAG tag, hexa-histidine, or the influenza HA tag. The affinity tag or reporter fusion joins the reading frames of SEQ ID NO: 1, 2, and/or 3 to the reading frame of the reporter gene encoding the affinity tag such that a translational fusion is generated. Expression of the fusion gene results in translation of a single polypeptide that includes both a nematode ATP synthase subunit E-like region and reporter protein or affinity tag. The fusion can also join a fragment of the reading frame of SEQ ID NO: 1, 2, and/or 3. The fragment can encode a functional region of the ATP synthase subunit E-like polypeptides, a structurally intact domain, or an epitope (e.g., a peptide of about 8, 10, 20, or 30 or more amino acids). A nematode ATP synthase subunit E-like nucleic acid that includes at least one of a regulatory region (e.g., a 5' regulatory region, a promoter, an enhancer, a 5' untranslated region, a translational start site, a 3' untranslated region, a polyadenylation site, or a 3' regulatory region) can also be fused to a heterologous nucleic acid. For example, the promoter of an ATP synthase subunit E-like nucleic acid can be fused to a heterologous nucleic acid, e.g., a nucleic acid encoding a reporter protein.

Suitable cells to transform include any cell that can be transformed with a nucleic acid molecule of the present invention. A transformed cell of the present invention is also herein referred to as a recombinant or transgenic cell. Suitable cells can either be untransformed cells or cells that have already been transformed with at least one nucleic acid molecule. Suitable cells for transformation according to the present invention can either be: (i) endogenously capable of expressing the ATP synthase subunit E-like protein or; (ii) capable of producing such protein after transformation with at least one nucleic acid molecule of the present invention.

In an exemplary embodiment, a nucleic acid of the invention is used to generate a transgenic nematode strain, e.g., a transgenic C. elegans strain. To generate such a strain, nucleic acid is injected into the gonad of a nematode, thus generating a heritable extrachromosomal array containing the nucleic acid (see, e.g., Mello et al. (1991) EMBO J. 10:3959-3970). The transgenic nematode can be propagated to generate a strain harboring the transgene. Nematodes of the strain can be used in screens to identify inhibitors specific for a M. javanica, H. glycines, and/or Z. punctata ATP synthase subunit E-like gene.

Oligonucleotides

Also provided are oligonucleotides that can form stable hybrids with a nucleic acid molecule of the present invention. The oligonucleotides can be about 10 to 200 nucleotides, about 15 to 120 nucleotides, or about 17 to 80 nucleotides in length, e.g., about 10, 20, 30, 40, 50, 60, 80, 100, 120 nucleotides in length. The oligonucleotides can be used as probes to identify nucleic acid molecules, primers to produce nucleic acid molecules, or therapeutic reagents to inhibit nematode ATP synthase subunit E-like protein activity or production (e.g., antisense, triplex formation, ribozyme, and/or RNA drug-based reagents). The present invention includes oligonucleotides of RNA (ssRNA and dsRNA), DNA, or derivatives of either. The invention extends to the use of such oligonucleotides to protect non-nematode organisms (for example e.g., plants and animals) from disease by reading the viability of infecting namatodes, e.g., using a technology described herein. Appropriate oligonucleotide-containing therapeutic compositions can be administered to a non-nematode organism using techniques known to those skilled in the art, including, but not limited to, transgenic expression in plants or animals.

Primer sequences can be used to amplify an ATP synthase subunit E-like nucleic acid or fragment thereof. For example, at least 10 cycles of PCR amplification can be used to obtain such an amplified nucleic acid. Primers can be at least about 8-40, 10-30 or 14-25 nucleotides in length, and can anneal to a nucleic acid "template molecule", e.g., a template molecule encoding an ATP synthase subunit E-like genetic sequence, or a functional part thereof, or its complementary sequence. The nucleic acid primer molecule can be any nucleotide sequence of at least 10 nucleotides in length derived from, or contained within sequences depicted in SEQ ID NO: 1, 2, and/or 3 and their complements. The nucleic acid template molecule may be in a recombinant form, in a virus particle, bacteriophage particle, yeast cell, animal cell, plant cell, fungal cell, or bacterial cell. A primer can be chemically synthesized by routine methods.

This invention embodies any ATP synthase subunit E-like sequences that are used to identify and isolate similar genes from other organisms, including nematodes, prokaryotic organisms, and other eukaryotic organisms, such as other animals and/or plants.

In another embodiment, the invention provides oligonucleotides that are specific for a *M. javanica, H. glycines*, and/or *Z. punctata* ATP synthase subunit E-like nucleic acid molecule. Such oligonucleotides can be used in a PCR test to determine if a *M. javanica, H. glycines*, and/or *Z. punctata* nucleic acid is present in a sample, e.g., to monitor a disease caused *M. javanica* and/or *H. glycines*.

Protein Production

Isolated ATP synthase subunit E-like proteins from nematodes can be produced in a number of ways, including production and recovery of the recombinant proteins and/or chemical synthesis of the protein. In one embodiment, an isolated nematode ATP synthase subunit E-like protein is produced by culturing a cell, e.g., a bacterial, fungal, plant, or animal cell, capable of expressing the protein, under conditions for effective production and recovery of the protein. The nucleic acid can be operably linked to a heterologous promoter, e.g., an inducible promoter or a constitutive promoter. Effective growth conditions are typically, but not necessarily, in liquid media comprising salts, water, carbon, nitrogen, phosphate sources, minerals, and other nutrients, but may be any solution in which ATP synthase subunit E-like proteins may be produced.

In one embodiment, recovery of the protein may refer to collecting the growth solution and need not involve additional steps of purification. Proteins of the present invention, however, can be purified using standard purification techniques, such as, but not limited to, affinity chromatography, thermaprecipitation, immunoaffinity chromatography, ammonium sulfate precipitation, ion exchange chromatography, filtration, electrophoresis, hydrophobic interaction chromatography, and others.

The ATP synthase subunit E-like polypeptide can be fused to an affinity tag, e.g., a purification handle (e.g., glutathione-S-reductase, hexa-histidine, maltose binding protein, dihydrofolate reductases, or chitin binding protein) or an epitope tag (e.g., c-myc epitope tag, FLAG™ tag, or influenza HA tag). Affinity tagged and epitope tagged proteins can be purified using routine art-known methods.

Antibodies Against ATP Synthase Subunit E-Like Polypeptides

Recombinant ATP synthase subunit E-like gene products or derivatives thereof can be used to produce immunologically interactive molecules, such as antibodies, or functional derivatives thereof. Useful antibodies include those that bind to a polypeptide that has substantially the same sequence as the amino acid sequences recited in SEQ ID NO: 4, 5, and/or 6, or that has at least 60% similarity over 50 or more amino acids to these sequences. In a preferred embodiment, the antibody specifically binds to a polypeptide having the amino acid sequence recited in SEQ ID NO: 4, 5, and/or 6. The antibodies can be antibody fragments and genetically engineered antibodies, including single chain antibodies or chimeric antibodies that can bind to more than one epitope. Such antibodies may be polyclonal or monoclonal and may be selected from naturally occurring antibodies or may be specifically raised to a recombinant ATP synthase subunit E-like protein.

Antibodies can be derived by immunization with a recombinant or purified ATP synthase subunit E-like gene or gene product. As used herein, the term "antibody" refers to an immunoglobulin, or fragment thereof. Examples of antibody fragments include F(ab) and F(ab')$_2$ fragments, particularly functional ones able to bind epitopes. Such fragments can be generated by proteolytic cleavage, e.g., with pepsin, or by genetic engineering. Antibodies can be polyclonal, monoclonal, or recombinant. In addition, antibodies can be modified to be chimeric, or humanized. Further, an antibody can be coupled to a label or a toxin.

Antibodies can be generated against a full-length ATP synthase subunit E-like protein, or a fragment thereof, e.g., an antigenic peptide. Such polypeptides can be coupled to an adjuvant to improve immunogenicity. Polyclonal serum is produced by injection of the antigen into a laboratory animal such as a rabbit and subsequent collection of sera. Alternatively, the antigen is used to immunize mice. Lymphocytic cells are obtained from the mice and fused with myelomas to form hybridomas producing antibodies.

Peptides for generating ATP synthase subunit E-like antibodies can be about 8, 10, 15, 20, 30 or more amino acid residues in length, e.g., a peptide of such length obtained from SEQ ID NO: 4, 5, and/or 6. Peptides or epitopes can also be selected from regions exposed on the surface of the protein, e.g., hydrophilic or amphipathic regions. An epitope in the vicinity of the active or binding site can be selected such that an antibody binding such an epitope would block access to the active site or prevent binding. Antibodies reactive with, or specific for, any of these regions, or other regions or domains described herein are provided. An antibody to an ATP synthase subunit E-like protein can modulate an ATP synthase subunit E-like activity.

Monoclonal antibodies, which can be produced by routine methods, are obtained in abundance and in homogenous form from hybridomas formed from the fusion of immortal cell lines (e.g., myelomas) with lymphocytes immunized with ATP synthase subunit E-like polypeptides such as those set forth in SEQ ID NO: 4, 5, and/or 6.

In addition, antibodies can be engineered, e.g., to produce a single chain antibody (see, for example, Colcher et al. (1999) *Ann N Y Acad Sci* 880: 263-280; and Reiter (1996) *Clin Cancer Res* 2: 245-252). In still another implementation, antibodies are selected or modified based on screening procedures, e.g., by screening antibodies or fragments thereof from a phage display library.

Antibodies of the present invention have a variety of important uses within the scope of this invention. For example, such antibodies can be used: (i) as therapeutic compounds to passively immunize an animal in order to protect the animal from nematodes susceptible to antibody treatment; (ii) as reagents in experimental assays to detect presence of nematodes; (iii) as tools to screen for expression of the gene product in nematodes, animals, fungi, bacteria, and plants; and/or (iv) as a purification tool of ATP synthase subunit E-like protein; (v) as ATP synthase subunit E inhibitors/activators that can be expressed or introduced into plants or animals for therapeutic purposes.

An antibody against an ATP synthase subunit E-like protein can be produced in a plant cell, e.g., in a transgenic plant or in culture (see, e.g., U.S. Pat. No. 6,080,560).

Antibodies that specifically recognize a *M. javanica, H. glycines*, and/or *Z. punctata* ATP synthase subunit E-like proteins can be used to identify *M. javanica, H. glycines*, and/or *Z. punctata* nematodes, and, thus, can be used to monitor a disease caused by *M. javanica* and/or *H. glycines*.

Nucleic Acids Agents

Also featured are isolated nucleic acids that are antisense to nucleic acids encoding nematode ATP synthase subunit E-like proteins. An "antisense" nucleic acid includes a sequence that is complementary to the coding strand of a nucleic acid encoding an ATP synthase subunit E-like protein. The complementarity can be in a coding region of the coding strand or in a noncoding region, e.g., a 5' or 3' untranslated region, e.g., the translation start site. The antisense nucleic acid can be produced from a cellular promoter (e.g., a RNA polymerase II or III promoter), or can be introduced into a cell, e.g., using a liposome. For example, the antisense nucleic acid can be a synthetic oligonucleotide having a length of about 10, 15, 20, 30, 40, 50, 75, 90, 120 or more nucleotides in length.

An antisense nucleic acid can be synthesized chemically or produced using enzymatic reagents, e.g., a ligase. An antisense nucleic acid can also incorporate modified nucleotides, and artificial backbone structures, e.g., phosphorothioate derivative, and acridine substituted nucleotides.

Ribozymes. The antisense nucleic acid can be a ribozyme. The ribozyme can be designed to specifically cleave RNA, e.g., an ATP synthase subunit E-like mRNA. Methods for designing such ribozymes are described in U.S. Pat. No. 5,093,246 or Haselhoff and Gerlach (1988) *Nature* 334:585-591. For example, the ribozyme can be a derivative of Tetrahymena L-19 IVS RNA in which the nucleotide sequence of the active site is modified to be complementary to an ATP synthase subunit E-like nucleic acid (see, e.g., Cech et al. U.S. Pat. No. 4,987,071; and Cech et al. U.S. Pat. No. 5,116,742).

Peptide Nucleic acid (PNA). An antisense agent directed against an ATP synthase subunit E-like nucleic acid can be a peptide nucleic acid (PNA). See Hyrup et al. (1996) *Bioorganic & Medicinal Chemistry* 4: 5-23) for methods and a description of the replacement of the deoxyribose phosphate backbone for a pseudopeptide backbone. A PNA can specifically hybridize to DNA and RNA under conditions of low ionic strength as a result of its electrostatic properties. The synthesis of PNA oligomers can be performed using standard solid phase peptide synthesis protocols as described in Hyrup et al. (1996) supra and Perry-O'Keefe et al. *Proc. Natl. Acad. Sci.* 93: 14670-14675.

RNA Mediated Interference (RNAi). A double stranded RNA (dsRNA) molecule can be used to inactivate an ATP synthase subunit E-like gene in a cell by a process known as RNA mediated-interference (RNAi; e.g., Fire et al. (1998) *Nature* 391:806-811, and Gönczy et al. (2000) *Nature* 408: 331-336). The dsRNA molecule can have the nucleotide sequence of an ATP synthase subunit E-like nucleic acid described herein or a fragment thereof. The molecule can be injected into a cell, or a syncytium, e.g., a nematode gonad as described in Fire et al., supra.

Screening Assays

Another embodiment of the present invention is a method of identifying a compound capable of altering (e.g., inhibiting or enhancing) the activity of ATP synthase subunit E-like molecules. This method, also referred to as a "screening assay," herein, includes, but is not limited to, the following procedure: (i) contacting an isolated ATP synthase subunit E-like protein with a test inhibitory compound under conditions in which, in the absence of the test compound, the protein has ATP synthase subunit E-like activity; and (ii) determining if the test compound alters the ATP synthase subunit E-like activity or alters the ability of the subunit E to regulate other polypeptides or molecules e.g., the catalytic subcomplex of ATP synthase or a portion (subunit) thereof. Suitable inhibitors or activators that alter a nematode ATP synthase subunit E-like activity include compounds that interact directly with a nematode ATP synthase subunit E-like protein, perhaps but not necessarily, in the active or binding site. They can also interact with other regions of the nematode ATP synthase subunit E protein by binding to regions outside of the active site or site responsible for regulation, for example, by allosteric interaction. They can also bind to the complex normally bound by the subunit E, interfering with binding to and regulation by the subunit E.

Compounds. A test compound can be a large or small molecule, for example, an organic compound with a molecular weight of about 100 to 10,000; 200 to 5,000; 200 to 2000; or 200 to 1,000 daltons. A test compound can be any chemical compound, for example, a small organic molecule, a carbohydrate, a lipid, an amino acid, a polypeptide, a nucleoside, a nucleic acid, or a peptide nucleic acid. Small molecules include, but are not limited to, metabolites, metabolic analogues, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds). Compounds and components for synthesis of compounds can be obtained from a commercial chemical supplier, e.g., Sigma-Aldrich Corp. (St. Louis, Mo.). The test compound or compounds can be naturally occurring, synthetic, or both. A test compound can be the only substance assayed by the method described herein. Alternatively, a collection of test compounds can be assayed either consecutively or concurrently by the methods described herein.

Compounds can also act by allosteric inhibition or by preventing the subunit E from binding to, and thus, regulating its target, i.e., an ATP synthase.

A high-throughput method can be used to screen large libraries of chemicals. Such libraries of candidate compounds can be generated or purchased, e.g., from Chembridge Corp. (San Diego, Calif.). Libraries can be designed to cover a diverse range of compounds. For example, a library can include 10,000, 50,000, or 100,000 or more unique compounds. Merely by way of illustration, a library can be constructed from heterocycles including pyridines, indoles, quinolines, furans, pyrimidines, triazines, pyrroles, imidazoles, naphthalenes, benzimidazoles, piperidines, pyrazoles, benzoxazoles, pyrrolidines, thiphenes, thiazoles, benzothiazoles, and morpholines. A library can be designed and synthesized to cover such classes of chemicals, e.g., as described in DeWitt et al. (1993) *Proc. Natl. Acad. Sci. U.S.A.* 90:6909-6913; Erb et al. (1994) *Proc. Natl. Acad. Sci. USA* 91:11422-11426; Zuckermann et al. (1994) *J. Med. Chem.* 37:2678-2685; Cho et al. (1993) Science 261:1303-1305; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233-1251.

Organism-based Assays. Organisms can be grown in microtiter plates, e.g., 6-well, 32-well, 64-well, 96-well, 384-well plates.

In one embodiment, the organism is a nematode. The nematodes can be genetically modified. Non-limiting examples of such modified nematodes include: 1) nematodes or nematode cells (*M. javanica, H. glycines, Z. punctata*, and/or *C. elegans*) having one or more ATP synthase subunit E-like genes inactivated (e.g., using RNA mediated interference); 2) nematodes or nematode cells expressing a heterologous ATP synthase subunit E-like gene, e.g., an ATP synthase subunit E-like gene from another species; and 3) nematodes or nematode cells having one or more endogenous ATP synthase subunit E-like genes inactivated and expressing a heterologous ATP synthase subunit E-like gene, e.g., a *M. javanica, H. glycines*, and/or *Z. punctata* ATP synthase subunit E-like gene as described herein.

A plurality of candidate compounds, e.g., a combinatorial library, can be screened. The library can be provided in a format that is amenable for robotic manipulation, e.g., in microtitre plates. Compounds can be added to the wells of the microtiter plates. Following compound addition and incubation, viability and/or reproductive properties of the nematodes or nematode cells are monitored.

The compounds can also be pooled, and the pools tested. Positive pools are split for subsequent analysis. Regardless of the method, compounds that decrease the viability or reproductive ability of nematodes, nematode cells, or progeny of the nematodes are considered lead compounds.

In another embodiment, the compounds can be tested on a microorganism or a eukaryotic or mammalian cell line, e.g., rabbit skin cells, Chinese hamster ovary cells (CHO), and/or Hela cells. For example, CHO cells absent for ATP synthase subunit E-like genes, but expressing a nematode ATP synthase subunit E-like gene can be used. The generation of such strains is routine in the art. As described above for nematodes and nematode cells, the cell lines can be grown in microtitre plates, each well having a different candidate compound or pool of candidate compounds. Growth is monitored during or after the assay to determine if the compound or pool of compounds is a modulator of a nematode ATP synthase subunit E-like polypeptide.

In Vitro Activity Assays. The screening assay can be an in vitro activity assay. For example, a nematode ATP synthase subunit E-like polypeptide can be purified as described above. The polypeptide can be disposed in an assay container, e.g., a well of a microtitre plate. A candidate compound can be added to the assay container, and the ATP synthase subunit E-like activity is measured. Optionally, the activity is compared to the activity measured in a control container in which no candidate compound is disposed or in which an inert or non-functional compound is disposed In Vitro Binding Assays. The screening assay can also be a cell-free binding assay, e.g., an assay to identify compounds that bind a nematode ATP synthase subunit E-like polypeptide. For example, a nematode ATP synthase subunit E-like polypeptide can be purified and labeled. The labeled polypeptide is contacted to beads; each bead has a tag detectable by mass spectroscopy, and test compound, e.g., a compound synthesized by combinatorial chemical methods. Beads to which the labeled polypeptide is bound are identified and analyzed by mass spectroscopy. The beads can be generated using "split-and-pool" synthesis. The method can further include a second assay to determine if the compound alters the activity of the ATP synthase subunit E-like polypeptide.

Optimization of a Compound. Once a lead compound has been identified, standard principles of medicinal chemistry can be used to produce derivatives of the compound. Derivatives can be screened for improved pharmacological properties, for example, efficacy, pharmacokinetics, stability, solubility, and clearance. The moieties responsible for a compound's activity in the above-described assays can be delineated by examination of structure-activity relationships (SAR) as is commonly practiced in the art. One can modify moieties on a lead compound and measure the effects of the modification on the efficacy of the compound to thereby produce derivatives with increased potency. For an example, see Nagarajan et al. (1988) *J. Antibiot.* 41:1430-1438. A modification can include N-acylation, amination, amidation, oxidation, reduction, alkylation, esterification, and hydroxylation. Furthermore, if the biochemical target of the lead compound is known or determined, the structure of the target and the lead compound can inform the design and optimization of derivatives. Molecular modeling software to do this is commercially available (e.g., Molecular Simulations, Inc.). "SAR by NMR," as described in Shuker et al. (1996) *Science* 274:1531-1534, can be used to design ligands with increased affinity, by joining lower-affinity ligands.

A preferred compound is one that interferes with the function of an ATP synthase subunit E-like polypeptide and that is not substantially toxic to plants, animals, or humans. By "not substantially toxic" it is meant that the compound does not substantially affect the respective animal, or human ATP synthase subunit E proteins or ATP synthase activity. Thus, particularly desirable inhibitors of *M. javanica, H. glycines*, and/or *Z. punctata* ATP synthase subunit E do not substantially inhibit ATP synthase subunit E-like polypeptides or ATP synthase activity of vertebrates, e.g., humans for example. Other desirable compounds do not substantially inhibit to ATP synthase activity of plants.

Standard pharmaceutical procedures can be used to assess the toxicity and therapeutic efficacy of a modulator of an ATP synthase subunit E-like activity. The LD50 (the dose lethal to 50% of the population) and the ED50 (the dose therapeutically effective in 50% of the population can be measured in cell cultures, experimental plants (e.g., in laboratory or field studies), or experimental animals. Optionally, a therapeutic index can be determined which is expressed as the ratio: LD50/ED50. High therapeutic indices are indicative of a compound being an effective ATP synthase subunit E-like inhibitor, while not causing undue toxicity or side effects to a subject (e.g., a host plant or host animal).

Alternatively, the ability of a candidate compound to modulate a non-nematode ATP synthase subunit E-like polypeptide is assayed, e.g., by a method described herein. For example, the inhibition constant of a candidate compound for a mammalian ATP synthase subunit E-like polypeptide can be measured and compared to the inhibition constant for a nematode ATP synthase subunit E-like polypeptide.

The aforementioned analyses can be used to identify and/or design a modulator with specificity for nematode ATP synthase subunit E-like polypeptide over vertebrate or other animal (e.g., mammalian) ATP synthase subunit E-like polypeptides. Suitable nematodes to target are any nematodes with the ATP synthase subunit E-like proteins or proteins that can be targeted by a compound that otherwise inhibits, reduces, activates, or generally effects the activity of nematode ATP synthase subunit E proteins.

Inhibitors of nematode ATP synthase subunit E-like proteins can also be used to identify ATP synthase subunit E-like proteins in the nematode or other organisms using procedures known in the art, such as affinity chromatography. For example, a specific antibody may be linked to a resin and a nematode extract passed over the resin, allowing any ATP synthase subunit E-like proteins that bind the antibody to bind the resin. Subsequent biochemical techniques familiar to those skilled in the art can be performed to purify and identify bound ATP synthase subunit E-like proteins.

Agricultural Compositions

A compound that is identified as an ATP synthase subunit E-like polypeptide inhibitor can be formulated as a composition that is applied to plants, soil, or seeds in order to confer nematode resistance. The composition can be prepared in a solution, e.g., an aqueous solution, at a concentration from about 0.005% to 10%, or about 0.01% to 1%, or about 0.1% to 0.5% by weight. The solution can include an organic solvent, e.g., glycerol or ethanol. The composition can be formulated with one or more agriculturally acceptable carriers. Agricultural carriers can include: clay, talc, bentonite, diatomaceous earth, kaolin, silica, benzene, xylene, toluene, kerosene, N-methylpyrrolidone, alcohols (methanol, ethanol, isopropanol, n-butanol, ethylene glycol, propylene glycol, and the like), and ketones (acetone, methylethyl ketone, cyclohexanone, and the like). The formulation can optionally further include stabilizers, spreading agents, wetting extenders, dispersing agents, sticking agents, disintegrators, and other additives, and can be prepared as a liquid, a water-soluble solid (e.g., tablet, powder or granule), or a paste.

Prior to application, the solution can be combined with another desired composition such as another antihelmintic agent, germicide, fertilizer, plant growth regulator and the like.

The solution may be applied to the plant tissue, for example, by spraying, e.g., with an atomizer, by drenching, by pasting, or by manual application, e.g., with a sponge. The solution can also be distributed from an airborne source, e.g., an aircraft or other aerial object, e.g., a fixture mounted with an apparatus for spraying the solution, the fixture being of sufficient height to distribute the solution to the desired plant tissues. Alternatively, the composition can be applied to plant tissue from a volatile or airborne source. The source is placed in the vicinity of the plant tissue and the composition is dispersed by diffusion through the atmosphere. The source and the plant tissue to be contacted can be enclosed in an incubator, growth chamber, or greenhouse, or can be in sufficient proximity that they can be outdoors.

If the composition is distributed systemically thorough the plant, the composition can be applied to tissues other than the leaves, e.g., to the stems or roots. Thus, the composition can be distributed by irrigation. The composition can also be injected directly into roots or stems.

A skilled artisan would be able to determine an appropriate dosage for formulation of the active ingredient of the composition. For example, the ED50 can be determined as described above from experimental data. The data can be obtained by experimentally varying the dose of the active ingredient to identify a dosage effective for killing a nematode, while not causing toxicity in the host plant or host animal (i.e. non-nematode animal).

A number of embodiments of the invention have been described. Nevertheless, it will be understood that various modifications may be made without departing from the spirit and scope of the invention. Accordingly, other embodiments are within the scope of the following claims.

---

What is claimed is:

1. A purified polypeptide comprising the amino acid sequence of SEQ ID NO:5.

2. A purified polypeptide consisting of the amino acid sequence of SEQ ID NO:5.

* * * * *